United States Patent
Abdolahad et al.

(10) Patent No.: US 11,079,355 B2
(45) Date of Patent: Aug. 3, 2021

(54) ULTRASOUND-ASSISTED ELECTROCHEMICAL DISTINCTION OF NORMAL AND CANCEROUS CELLS

(71) Applicants: Mohammad Abdolahad, Tehran (IR); Mohammad Ali Khayamian, Tehran (IR); Saeid Ansaryan, Ilam (IR); Majid Baniassadi, Tehran (IR)

(72) Inventors: Mohammad Abdolahad, Tehran (IR); Mohammad Ali Khayamian, Tehran (IR); Saeid Ansaryan, Ilam (IR); Majid Baniassadi, Tehran (IR)

(73) Assignee: NANO HESGARSAZAN SALAMAT ARYA, Tehran (IR)

(*) Notice: Subject to any disclaimer, the term of this patent is extended or adjusted under 35 U.S.C. 154(b) by 105 days.

(21) Appl. No.: 15/960,542

(22) Filed: Apr. 23, 2018

(65) Prior Publication Data

US 2018/0252677 A1    Sep. 6, 2018

Related U.S. Application Data

(60) Provisional application No. 62/488,873, filed on Apr. 24, 2017, provisional application No. 62/488,875, filed on Apr. 24, 2017.

(51) Int. Cl.
   *G01N 27/48*  (2006.01)
   *G01N 27/327* (2006.01)
   (Continued)

(52) U.S. Cl.
   CPC ......... *G01N 27/48* (2013.01); *A61B 5/1473* (2013.01); *C23C 14/0005* (2013.01);
   (Continued)

(58) Field of Classification Search
   CPC .................. G01N 27/48; G01N 33/4833
   See application file for complete search history.

(56) References Cited

U.S. PATENT DOCUMENTS 8,097,148 B2 *  1/2012  Dietze .................. G01N 27/38
                                                       204/402
8,956,525 B2 *  2/2015  Gerken ............... C25B 11/0489
                                                       205/630
(Continued)

OTHER PUBLICATIONS

Md. Abdul Kafi et al., Electrochemical cell-based chip for the detection of toxic effects of bisphenol-A on neuroblastoma cells, Biosensors and Bioelectronics, 2011,3371-3375, vol. 26, Elsevier.
(Continued)

*Primary Examiner* — Luan V Van
*Assistant Examiner* — Caitlyn Mingyun Sun
(74) *Attorney, Agent, or Firm* — Bajwa IP Law Firm; Haris Zaheer Bajwa

(57) ABSTRACT

A method for cancer diagnosis is disclosed. The method includes forming a plurality of cultured cells on an electrochemical biosensor placing the electrochemical biosensor in a medium solution comprising a cell culture solution of a plurality of biological cells, measuring a first electrochemical response from the electrochemical biosensor with the plurality of cultured cells, forming a plurality of stimulated cells on the electrochemical biosensor by ultrasonically stimulating of the plurality of cultured cells, measuring a second electrochemical response from the electrochemical biosensor with the plurality of stimulated cells, and detecting presence of cancer cells responsive to a difference between the first electrochemical response and the second electrochemical response being less than a threshold. Where, the first electrochemical response includes an electrochemical response of the plurality of cultured cells and the second
(Continued)

electrochemical response includes an electrochemical response of the plurality of stimulated cells.

12 Claims, 32 Drawing Sheets

(51) Int. Cl.
| | |
|---|---|
| G01N 33/483 | (2006.01) |
| C23C 14/02 | (2006.01) |
| C23C 14/58 | (2006.01) |
| C23C 14/34 | (2006.01) |
| G03F 7/20 | (2006.01) |
| C23C 14/20 | (2006.01) |
| C25B 9/17 | (2021.01) |
| C25B 11/051 | (2021.01) |
| C25B 11/057 | (2021.01) |
| C25B 11/091 | (2021.01) |
| A61B 5/1473 | (2006.01) |
| C23C 14/00 | (2006.01) |
| C25B 1/02 | (2006.01) |
| G01N 33/49 | (2006.01) |

(52) U.S. Cl.
CPC .......... *C23C 14/022* (2013.01); *C23C 14/205* (2013.01); *C23C 14/3464* (2013.01); *C23C 14/5806* (2013.01); *C23C 14/5846* (2013.01); *C25B 1/02* (2013.01); *C25B 9/17* (2021.01); *C25B 11/051* (2021.01); *C25B 11/057* (2021.01); *C25B 11/091* (2021.01); *G01N 27/327* (2013.01); *G01N 33/4833* (2013.01); *G01N 33/49* (2013.01); *G03F 7/70* (2013.01)

(56) References Cited

U.S. PATENT DOCUMENTS

| | | | | |
|---|---|---|---|---|
| 8,962,270 | B2* | 2/2015 | Malecha | G01N 33/49 |
| | | | | 435/14 |
| 8,992,958 | B2* | 3/2015 | Kanehira | B82Y 5/00 |
| | | | | 424/405 |
| 9,213,013 | B2* | 12/2015 | Zevenbergen | G01N 27/4045 |
| 9,447,384 | B2* | 9/2016 | Cass | C12Q 1/005 |
| 2009/0050492 | A1 | 2/2009 | Alocilja et al. | |
| 2010/0095580 | A1* | 4/2010 | Suzuki | C10L 1/328 |
| | | | | 44/301 |
| 2016/0258899 | A1* | 9/2016 | Patolsky | G01N 33/50 |

OTHER PUBLICATIONS

Chunmei Yu et al., A new disposable electrode for electrochemical study of leukemia K562 cells and anticancer drug sensitivity test, Biosensors and Bioelectronics, 2014, 142-147, vol. 53, Elsevier.

Truong An Tran, Characterization of Cell Membrane Response to Ultrasound Activated Microbubbles, ieee transactions on ultrasonics, ferroelectrics, and frequency control, Jan. 2008, pp. 44-49, vol. 55, No. 1.

Spiros Kotopoulis, Treatment of human pancreatic cancer using combined ultrasound, microbubbles, and gemcitabine: A clinical case study, Medical Physics, 2013, pp. 072902-1 to 072902-9, vol. 40.

Z. Fan, Intracellular Delivery and Calcium Transients Generated in Sonoporation Facilitated by Microbubbles, J Control Release, Feb. 25, 2010, pp. 1-20, vol. 142 (1): 31.

* cited by examiner

1102

1106

ULTRASOUND-ASSISTED ELECTROCHEMICAL DISTINCTION OF NORMAL AND CANCEROUS CELLS

CROSS-REFERENCE TO RELATED APPLICATION

This application claims the benefit of priority from pending U.S. Provisional Patent Application Ser. No. 62/488,873 filed on Apr. 24, 2017, and entitled "ELECTROCHEMICAL APPROACH FOR SENSING SONOPORATION OF A CELL" and pending U.S. Provisional Patent Application Ser. No. 62/488,875 filed on Apr. 24, 2017, and entitled "ULTRASOUND-ASSISTED ELECTROCHEMICAL DISTINCTION OF NORMAL AND CANCEROUS CELLS", which are both incorporated herein by reference in their entirety.

SPONSORSHIP STATEMENT

This application has been sponsored by Iran Patent Office, which does not have any rights in this application.

TECHNICAL FIELD

The present disclosure generally relates to cancer diagnosis, and particularly, to a method for cancer diagnosis via monitoring electrochemical responses of cells before and after ultrasonic stimulation (sonoporation) of cells.

BACKGROUND

Low intensity ultrasound waves have been explored in various contexts in medical applications such as sonodynamic therapy, non-thermal therapy and diagnosis for decades. Upsurge in membrane penetrability, uptake of various drugs and therapeutic compounds and rush of ions into or out of the cells are all the consequences of the sonoporation phenomenon as the main bioeffects of ultrasonic stimulation (US) of the cells. Moreover, microbubble generation is a crucial pre-step of sonoporation. Even though the microbubbles are produced inherently in the process of ultrasonic stimulation, commercial types of microbubble contrast agents (polymeric microspheres) are applied in most US-based studies to lessen the threshold of cavitation and augment the subsequent sonoporation efficiency.

Monitoring the biological response of the cells to ultrasonic stimulation is an important step in evaluating sonoporation process. Moreover, cells may exhibit different ionic functions during their phenotypic changes. So, ion exchanging activities of different cells due to US would be induced from their phenotypes. Investigation of cellular disorders based on material exchanges was reviewed by many researchers. Therefore, analyzing the response of the normal and cancer cells to sonoporation may lead to a diagnostic indication correlated with ion exchange parameters of the cell.

Hence, there is a need for a fast, cost-effective, label free method and system for diagnosis of cancer cells from that of normal phenotypes by monitoring the sonoporation induced ionic exchanges confirmed by membrane voltage dissimilarities in the cells. So there is a need for a clinical-appropriate and accurate electrochemical biosensor for electrochemical analyzes in the presence of ultrasonic stimulation of cells to detect the cancer cells if exist. In addition, there is a need for biocompatible microbubbles for utilizing in such methods and systems to enhance the sonoporation effect on cells.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for cancer diagnosis. The method may include forming a plurality of cultured cells on an electrochemical biosensor by placing the electrochemical biosensor in a medium solution comprising a cell culture solution of a plurality of biological cells, measuring a first electrochemical response from the electrochemical biosensor with the plurality of cultured cells, forming a plurality of stimulated cells on the electrochemical biosensor by ultrasonically stimulating of the plurality of cultured cells, measuring a second electrochemical response from the electrochemical biosensor with the plurality of stimulated cells, and detecting presence of cancer cells responsive to a difference between the first electrochemical response and the second electrochemical response being less than a threshold. The first electrochemical response may include an electrochemical response of the plurality of cultured cells and the second electrochemical response may include an electrochemical response of the plurality of stimulated cells.

In an exemplary implementation, each of the first electrochemical response and the second electrochemical response may include an electrical current and the difference between the first electrochemical response and the second electrochemical response may include $\Delta I/I$ that may be defined by: $\Delta I/I = (I\_(US\ off) - I\_(US\ on))/I\_(US\ off)$, where $I\text{US off}$ may include the first electrochemical response and $I\text{US on}$ may include the second electrochemical response.

In an exemplary implementation, the threshold may include a value of about 0.05 for the ultrasonic waves with an intensity of less than about 1 W/cm$^2$ and a duration of less than about 5 seconds. In another exemplary implementation, the threshold may include a value of about 0.015 for the ultrasonic waves with an intensity of more than about 1 W/cm$^2$ and a duration of less than about 5 seconds.

In an exemplary implementation, each of the measuring the first electrochemical response from the electrochemical biosensor with the plurality of cultured cells and measuring the second electrochemical response from the electrochemical biosensor with the plurality of stimulated cells may include measuring an electrochemical response via a cyclic voltammetry (CV) technique using an electrochemical stimulator-analyzer system. In an exemplary embodiment, the electrochemical stimulator-analyzer system may include a potentiostat.

In an exemplary implementation, forming the plurality of cultured cells on the electrochemical biosensor may include placing the electrochemical biosensor at the bottom of a chamber and filling the chamber with the medium solution, where the medium solution may include a cell culture solution of the plurality of biological cells.

In an exemplary implementation, the method may further include generating a plurality of microbubbles on the electrochemical biosensor with the plurality of cultured cells.

Generating the plurality of microbubbles on the electrochemical biosensor with the plurality of cultured cells may include electrolysis of the medium solution by applying an instantaneous electrical potential to the electrochemical biosensor with the plurality of cultured cells via a cyclic voltammetry technique using the electrochemical stimulator-analyzer system. In an exemplary embodiment, generating the plurality of microbubbles on the electrochemical biosensor with the plurality of cultured cells may include applying a DC signal with a voltage between about −2 V and about −0.5 V for a time duration less than about 1 seconds on the biosensor with the plurality of cultured cells using a potentiostat device.

In an exemplary implementation, forming the plurality of stimulated cells on the electrochemical biosensor by ultrasonically stimulating of the plurality of cultured cells using the ultrasonic system may include ultrasonically stimulating of the plurality of cultured cells responsive to applying ultrasonic waves to the plurality of cultured cells on the electrochemical biosensor in the medium solution and inducing an acoustic cavitation in the plurality of cultured cells by the plurality of microbubbles responsive to applying ultrasonic waves to the plurality of microbubbles on the electrochemical biosensor in the medium solution.

In an exemplary implementation, forming the plurality of stimulated cells on the electrochemical biosensor by ultrasonically stimulating of the plurality of cultured cells using the ultrasonic system may include exposing the medium solution containing the electrochemical biosensor with the plurality of cultured cells to an ultrasonic system and applying ultrasonic waves to the medium solution with a frequency range between about 10 KHz and about 100 KHz for a time duration between about 2 s and about 10 s to the plurality of cultured cells using the ultrasonic system. In an exemplary embodiment, subjecting the medium solution containing the electrochemical biosensor with the plurality of cultured cells to the ultrasonic system may include placing an ultrasonic horn above the electrochemical biosensor with the plurality of cultured cells and the ultrasonic horn may be connected to an ultrasonic generator. In an exemplary embodiment, ultrasonic stimulating of the plurality of cultured cells may include applying ultrasonic waves using the ultrasonic system with an intensity between about 0.5 w/cm$^2$ and about 5 w/cm$^2$.

In an exemplary implementation, the electrochemical biosensor may include a substrate layer with a nanoroughened surface and an integrated three-electrodes array. The integrated three-electrodes array may include a working electrode, a reference electrode and a counter electrode. The integrated three-electrodes array may include a Gold/Titanium (Au/Ti) bilayer being patterned on the nanoroughened surface.

In an exemplary embodiment, forming the plurality of cultured cells on the electrochemical biosensor may include culturing the plurality of biological cells on the working electrode. In an exemplary embodiment, the first electrochemical response may include an electrical current passing between the working electrode and the counter electrode in the presence of the plurality of cultured cells and the second electrochemical response may include an electrical current passing between the working electrode and the counter electrode in the presence of the plurality of stimulated cells.

In an exemplary implementation, the method may further include fabricating the electrochemical biosensor. Fabricating the electrochemical biosensor may include forming a nanoroughened surface on a substrate by treating the substrate using a reactive ion etching (RIE) system, depositing a Gold/Titanium (Au/Ti) bilayer on the nanoroughened surface and patterning a reference electrode, a counter electrode and a working electrode on the Au/Ti bilayer using photolithography technique. Depositing a Gold/Titanium (Au/Ti) bilayer on the nanoroughened surface may include depositing a Ti layer on the nanoroughened surface using Radio Frequency (RF) sputtering system and depositing an Au layer on the Ti layer using the Radio Frequency (RF) sputtering system.

In another aspect of the present disclosure, an electrochemical-ultrasonic system for electrochemical analysis of sonoporation of biological cells is disclosed. The electrochemical-ultrasonic system may include an electrochemical biosensor, an electrochemical stimulator-analyzer system, an ultrasonic system and a medium solution. The electrochemical biosensor may include a working electrode, a reference electrode and a counter electrode. The electrochemical stimulator-analyzer system may be connected to the electrochemical stimulator-analyzer system. The ultrasonic system may include an ultrasonic horn placed above the working electrode and an ultrasonic generator connected to the ultrasonic horn. The medium solution may include a plurality of biological cells in a cell culture solution, where the electrochemical biosensor in placed in the medium solution and the plurality of biological cells are cultured on the working electrode.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
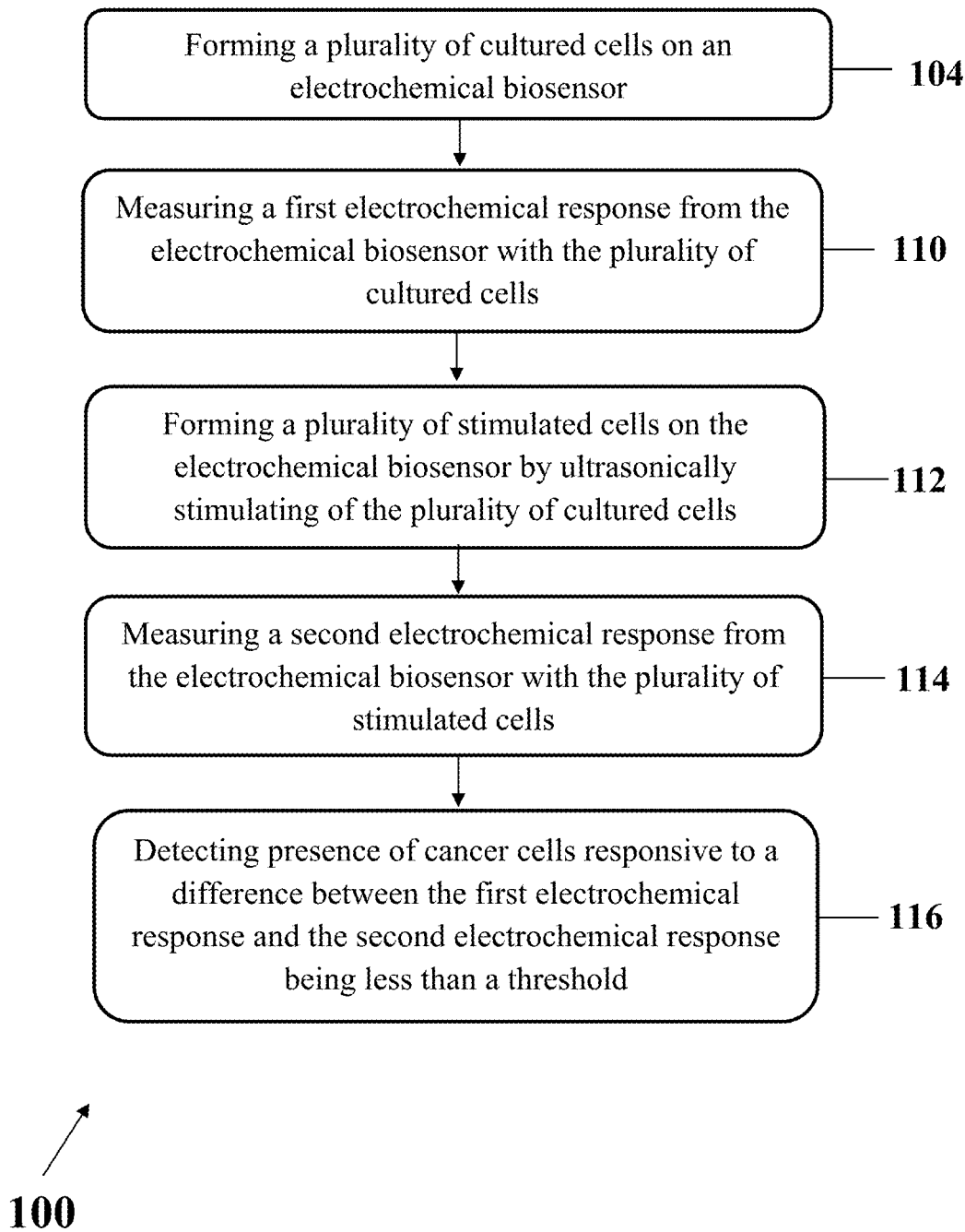
FIG. 1A illustrates an exemplary implementation of a method for cancer diagnosis, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Sonoporation of cells, which includes ultrasonic stimulation (US) of biological cells and forming sonopores in cell's membrane may be utilized for diagnostic, drug delivery and therapeutic fields of medicine. Ultrasonic stimulation of cells makes sonoporation in the cells which exchange ionic species between inner and outer parts of the membrane. Herein, such ionic variations in culture media are monitored and detected by cyclic voltammetry (CV) measurements. The differences in the CV patterns of the normal and cancerous cells before and after US may be related to the changed ion gradient between inner and outer parts of the cells that may be utilized to achieve a fast and simple label free method for cancer diagnosis.

Disclosed herein may include a simple method for cancer diagnosis via preparing an integrated electrochemical-ultrasonic system to ultrasonically stimulating cells and monitoring ion exchanges of cells before and after US by cyclic voltammetry analysis. An electrochemical biosensor with integrated three-electrodes array on a nanoroughened PMMA substrate may be designed and fabricated through the method to analyze the ultrasonically stimulated electrochemical response of cells. Cyclic voltammetry also generates microbubbles which improve the sonoporation efficacy as the main bioeffect of US on cells. Microbubbles generation may be achieved by applying a rapid electrical potential to the electrochemical biosensor. The method may utilize a cell culture solution as a media for cells culturing on the electrochemical biosensor as well as a media for CV measurements and ultrasonic waves propagation.

FIG. 1A shows an exemplary implementation of method 100 for cancer diagnosis, consistent with one or more exemplary embodiments of the present disclosure. Method 100 may include forming a plurality of cultured cells on an electrochemical biosensor by placing the electrochemical biosensor in a medium solution comprising a cell culture solution of a plurality of biological cells (step 104), measuring a first electrochemical response from the electrochemical biosensor with the plurality of cultured cells (step 110), forming a plurality of stimulated cells on the electrochemical biosensor by ultrasonically stimulating of the plurality of cultured cells (step 112), measuring a second electrochemical response from the electrochemical biosensor with the plurality of stimulated cells (step 114), and detecting presence of cancer cells responsive to a difference between the first electrochemical response and the second electrochemical response being less than a threshold (step 116). The first electrochemical response may include an electrochemical response of the plurality of cultured cells and the second electrochemical response may include an electrochemical response of the plurality of stimulated cells. In an exemplary embodiment, exemplary method 100 may be utilized for detection of any type of cancer, such as Breast cancer, Colon cancer, Ovarian cancer, Lung cancer, Prostate cancer, Bladder cancer, Skin cancer, Melanoma, Kidney cancer, Liver cancer, Cervical cancer, Pancreas cancer, etc.

Figure 1B:
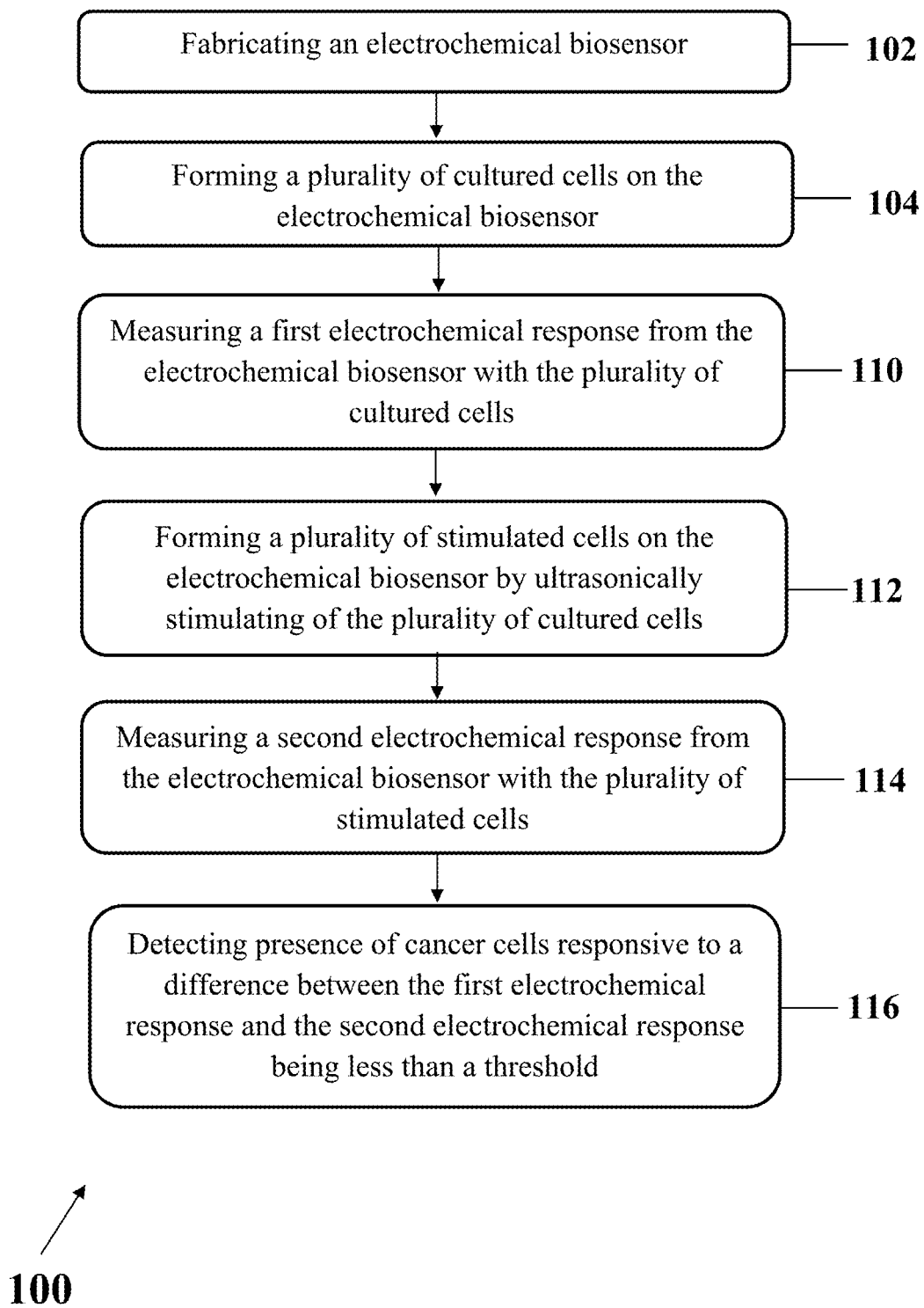
FIG. 1B illustrates another exemplary implementation of a method for cancer diagnosis, consistent with one or more exemplary embodiments of the present disclosure.

FIG. 1B shows another exemplary implementation of method 100 for cancer diagnosis, consistent with one or more exemplary embodiments of the present disclosure. Referring to FIG. 1B, method 100 may further include fabricating the electrochemical biosensor (step 102). Method 100 may include fabricating an electrochemical biosensor (step 102), forming a plurality of cultured cells on the electrochemical biosensor by placing the electrochemical biosensor in a medium solution comprising a cell culture solution of a plurality of biological cells (step 104), measuring a first electrochemical response from the electrochemical biosensor with the plurality of cultured cells (step 110), forming a plurality of stimulated cells on the electrochemical biosensor by ultrasonically stimulating of the plurality of cultured cells (step 112), measuring a second electrochemical response from the electrochemical biosensor with the plurality of stimulated cells (step 114), and detecting presence of cancer cells responsive to a difference between the first electrochemical response and the second electrochemical response being less than a threshold (step 116). The first electrochemical response may include an electrochemical response of the plurality of cultured cells and the second electrochemical response may include an electrochemical response of the plurality of stimulated cells.

Figure 1C:
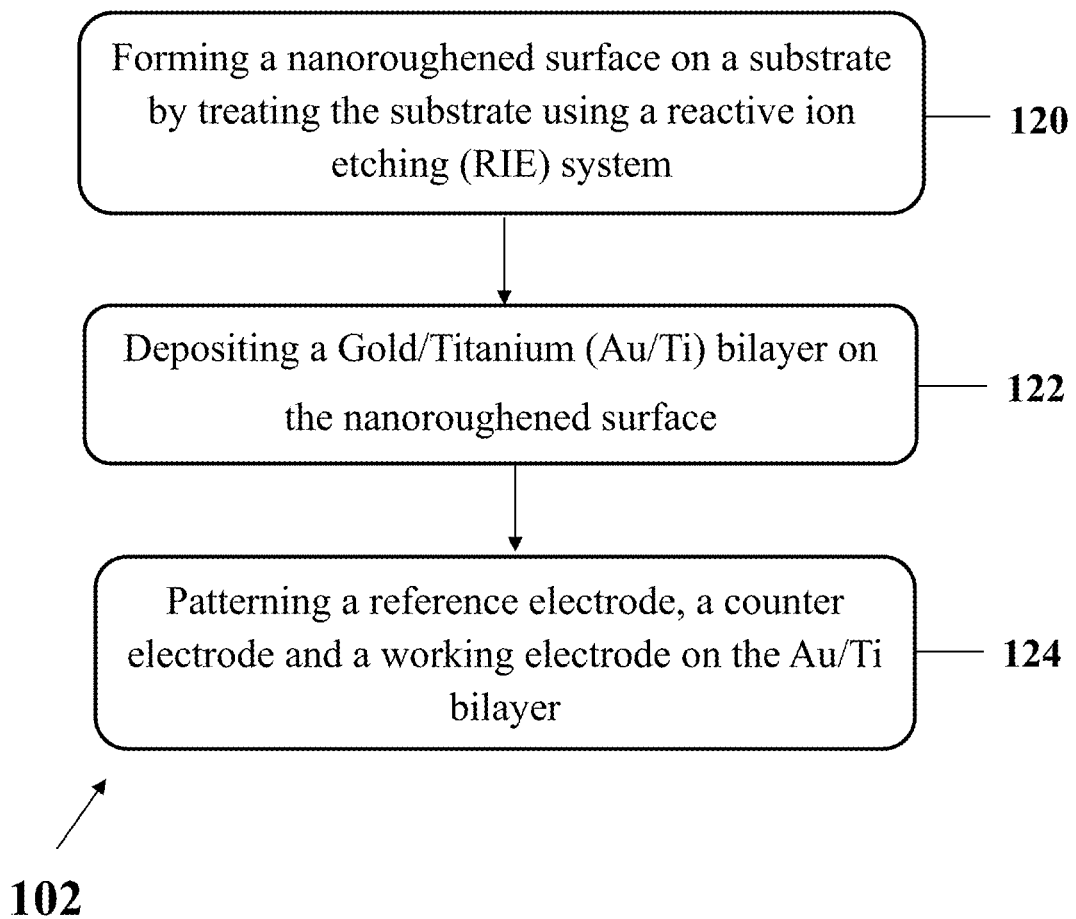
FIG. 1C illustrates an exemplary process for fabricating the electrochemical biosensor, consistent with one or more exemplary embodiments of the present disclosure.

Step 102 may include fabricating the electrochemical biosensor. FIG. 1C illustrates an exemplary implementation of step 102 representing an exemplary process for fabricating the electrochemical biosensor, consistent with one or more exemplary embodiments of the present disclosure. Step 102 may include forming a nanoroughened surface on a substrate by treating the substrate using a reactive ion etching (RIE) system (step 120), depositing a Gold/Titanium (Au/Ti) bilayer on the nanoroughened surface (step 122) and patterning a reference electrode, a counter electrode and a working electrode on the Au/Ti bilayer using photolithography technique (step 124).

Step 120 may include forming the nanoroughened surface on the substrate by treating the substrate using the reactive ion etching (RIE) system. In an exemplary embodiment, the substrate may include Poly(methyl methacrylate) (PMMA). In an exemplary embodiment, a surface of the substrate may be treated by a reactive ion etching (RIE) equipment in the presence of $SF_6$, $H_2$ and $O_2$ gases and in the existence of RF Plasma; thereby, forming the nanoroughened surface. The nanoroughened surface may have a roughness of less than about 100 nm, which may improve the quality and accuracy of electrochemical responses from the electrochemical biosensor.

Step 122 may include depositing the Gold/Titanium (Au/Ti) bilayer on the nanoroughened surface, which may be formed in step 120. In an exemplary embodiment, step 122 may include depositing a Ti layer on the nanoroughened surface using a Radio Frequency (RF) sputtering system and depositing an Au layer on the Ti layer using the Radio Frequency (RF) sputtering system. In an exemplary embodiment, depositing the Ti layer on the nanoroughened surface may include coating the nanoroughened surface of the substrate with a layer of Ti with a thickness of less than 10 mm. The Ti layer may include a thin layer that may be deposited on the nanoroughened surface in order to promote the adherence of the Au layer to the nanoroughened surface. In an exemplary embodiment, depositing the Au layer on the Ti layer may include coating the Ti layer with the Au layer with a thickness of less than about 50 nm.

Step 124 may include patterning the reference electrode, the counter electrode and the working electrode on the Au/Ti bilayer using photolithography technique. In an exemplary embodiment, step 124 may include patterning an integrated three-electrodes array with a desired pattern, for example, a circular pattern on the nanoroughened substrate coated with the Au/Ti bilayer. The integrated three-electrodes array including the reference electrode, the counter electrode and the working electrode may be projected on the Au/Ti bilayer via a photolithography technique.

Figure 2A:
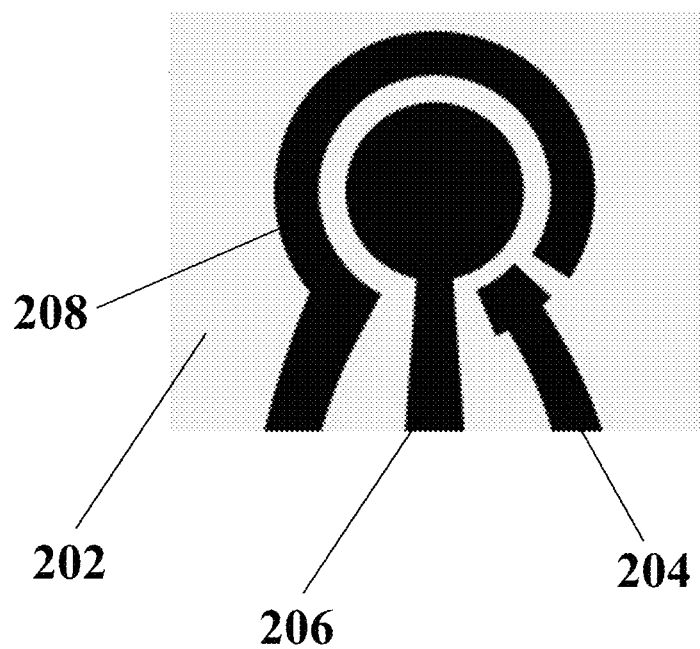
FIG. 2A illustrates a schematic top view of an exemplary electrochemical biosensor with a circular-patterned three-electrodes array, consistent with one or more exemplary embodiments of the present disclosure.

FIG. 2A shows a schematic top view of an exemplary electrochemical biosensor with a circular-patterned three-electrodes array on exemplary nanoroughened surface 202, consistent with one or more exemplary embodiments of the present disclosure. The circular-patterned three-electrodes array may include the reference electrode 204, the working electrode 206, and the counter electrode 208.

Figure 2B:
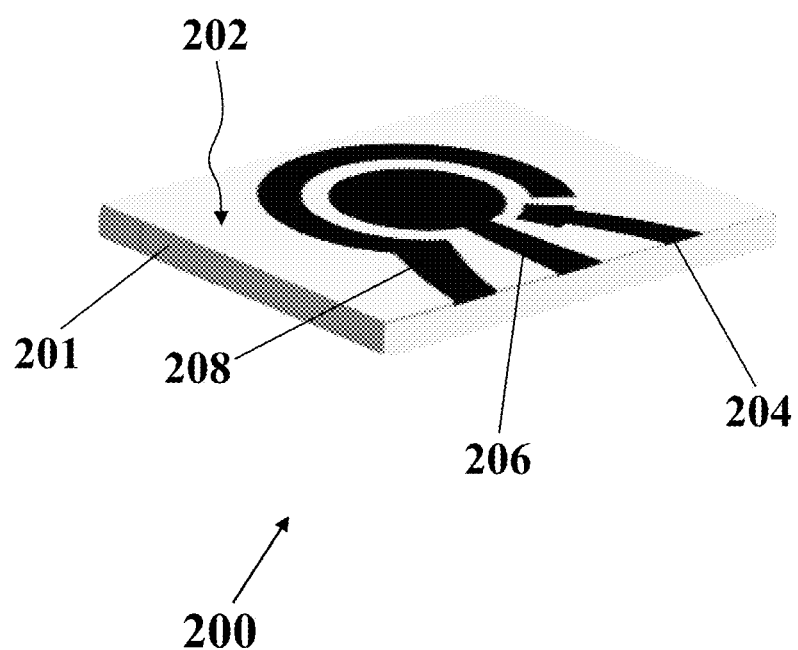
FIG. 2B illustrates a schematic view of an exemplary electrochemical biosensor, consistent with one or more exemplary embodiments of the present disclosure.

FIG. 2B shows a schematic view of an exemplary electrochemical biosensor 200, consistent with one or more exemplary embodiments of the present disclosure. Exemplary electrochemical biosensor 200 may include exemplary substrate 201 with nanoroughened surface 202 and an integrated three-electrodes array, which may include the reference electrode 204, the working electrode 206, and the counter electrode 208. The integrated three-electrodes array may include a Gold/Titanium (Au/Ti) bilayer that may be patterned on the nanoroughened surface 202.

Referring to FIGS. 1A and 1B, step 104 may include forming the plurality of cultured cells on exemplary electrochemical biosensor by placing the electrochemical biosensor in a medium solution comprising a cell culture solution of a plurality of biological cells. In an exemplary implementation, forming the plurality of cultured cells on an electrochemical biosensor may include culturing the plurality of biological cells on exemplary electrochemical biosensor 200 (FIG. 2B).

Figure 3A:
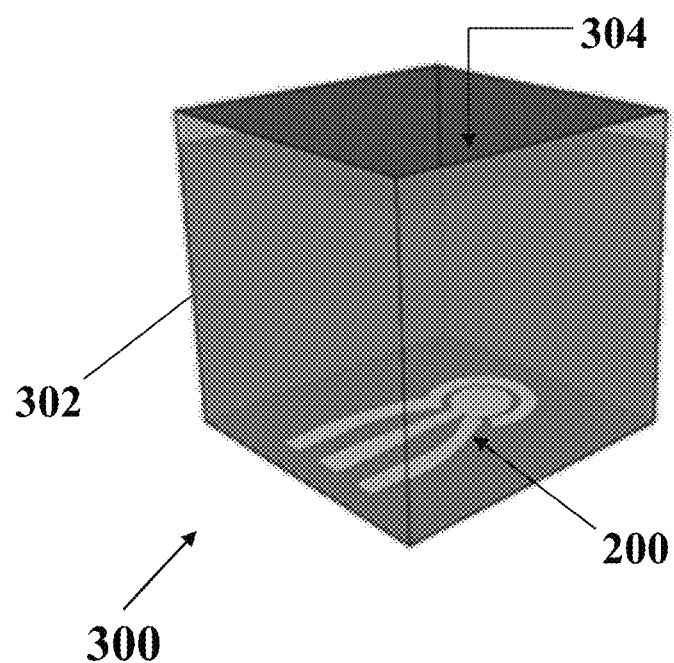
FIG. 3A illustrates a schematic view of an exemplary implementation of a setup prepared for conducting preparing the plurality of cultured cells on an exemplary electrochemical biosensor, consistent with one or more exemplary embodiments of the present disclosure.

FIG. 3A shows a schematic view of an exemplary implementation of a setup 300 prepared for conducting step 104 including forming the plurality of cultured cells on exemplary electrochemical biosensor 200, consistent with one or more exemplary embodiments of the present disclosure. In an exemplary implementation, forming the plurality of cultured cells on exemplary electrochemical biosensor 200 may include placing exemplary electrochemical biosensor 200 at the bottom of a chamber 302 and filling the chamber with a medium solution 304. The medium solution 304 may include a cell culture solution of the plurality of biological cells. In an exemplary embodiment, the medium solution 304 may include the plurality of biological cells in a Roswell Park Memorial Institute (RPMI) medium containing fetal bovine serum (FBS) and antibiotics.

In an exemplary implementation, the plurality of biological cells may be cultured on exemplary working electrode 206 of exemplary electrochemical biosensor 200. In an exemplary embodiment, an area of exemplary electrochemical biosensor 200 including working electrode 206 may be isolated from the rest parts of exemplary electrochemical biosensor 200, for example, by a silicone gasket separator. Subsequently, the plurality of biological cells may be seeded on working electrode 206 and exemplary electrochemical biosensor 200 may be incubated overnight. Consequently, the plurality of cultured cells may be attached on working electrode 206. Then, the silicone gasket separator may be replaced with a bigger separator in in order to the medium solution may be in touch with all three electrodes of reference electrode 204, working electrode 206, and counter electrode 208.

Referring to FIGS. 1A and 1B, step 110 may include measuring the first electrochemical response from the electrochemical biosensor with the plurality of cultured cells. Step 110 may include connecting exemplary electrochemical biosensor 200 with the plurality of cultured cells that may be obtained from step 104 to an electrochemical stimulator-analyzer system, and measuring the first electrochemical response from exemplary electrochemical biosensor 200 with the plurality of cultured cells. The electrochemical stimulator-analyzer system may be configured to measure electrochemical responses from exemplary electrochemical biosensor 200.

Figure 3B:
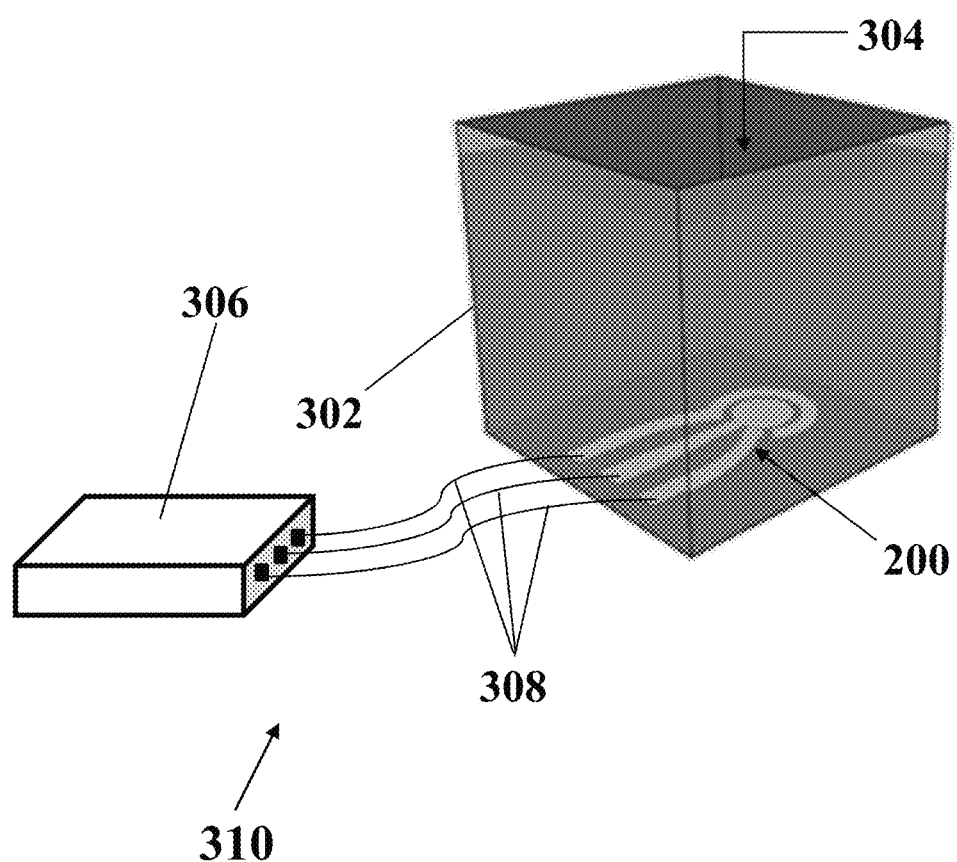
FIG. 3B illustrates a schematic view of an exemplary implementation of exemplary electrochemical system prepared by connecting exemplary electrochemical biosensor to an exemplary electrochemical stimulator-analyzer system, consistent with one or more exemplary embodiments of the present disclosure.

In an exemplary implementation, connecting exemplary electrochemical biosensor 200 with the plurality of cultured cells that may be obtained from step 104 to the electrochemical stimulator-analyzer system may result in preparation of an electrochemical system. FIG. 3B shows a schematic view of an exemplary implementation of the electrochemical system 310 that may be prepared by connecting exemplary electrochemical biosensor 200 to an exemplary electrochemical stimulator-analyzer system 306, consistent with one or more exemplary embodiments of the present disclosure. Exemplary electrochemical biosensor 200 may be connected to exemplary electrochemical stimulator-analyzer system 306 via electrical connectors 308.

In an exemplary implementation, exemplary electrochemical stimulator-analyzer system 306 may include a device utilizing cyclic voltammetry (CV) technique for electrochemical measurements and analyzes. In an exemplary embodiment, exemplary electrochemical stimulator-analyzer system 306 may include a potentiostat device.

Referring to FIGS. 1A and 1B, step 110 may include measuring the first electrochemical response from the electrochemical biosensor with the plurality of cultured cells, where the first electrochemical response may include an electrochemical response of the plurality of cultured cells on the electrochemical biosensor. In an exemplary implementation of step 110 and referring to FIG. 3B, the first electrochemical response may be measured form electrochemical biosensor 200 with the plurality of cultured cells by exemplary electrochemical stimulator-analyzer system 306 utilizing electrochemical system 310.

In an exemplary embodiment, measuring the first electrochemical response from exemplary electrochemical biosensor 200 with the plurality of cultured cells may include measuring an electrochemical response via the cyclic voltammetry (CV) technique using exemplary electrochemical stimulator-analyzer system 306. The medium solution 304 may include an electrolyte solution for CV measurements as well as a culture solution in step 104. The first electrochemical response may include an electrical current, which may include an electrical current passing between exemplary working electrode 206 and counter electrode 208 in the presence of the plurality of cultured cells on exemplary electrochemical biosensor 200.

Referring to FIGS. 1A and 1B, step 112 may include forming the plurality of stimulated cells on exemplary electrochemical biosensor 200 by ultrasonically stimulating of the plurality of cultured cells. In an exemplary implementation, ultrasonic stimulation of the plurality of cultured cells may include applying ultrasonic waves on the plurality of cultured cells on exemplary electrochemical biosensor 200 using an ultrasonic system; thereby, resulting in ultrasonically stimulating (sonoporation) of the plurality of cultured cells on exemplary electrochemical biosensor 200. Consequently, the plurality of stimulated cells may be formed.

Figure 3C:
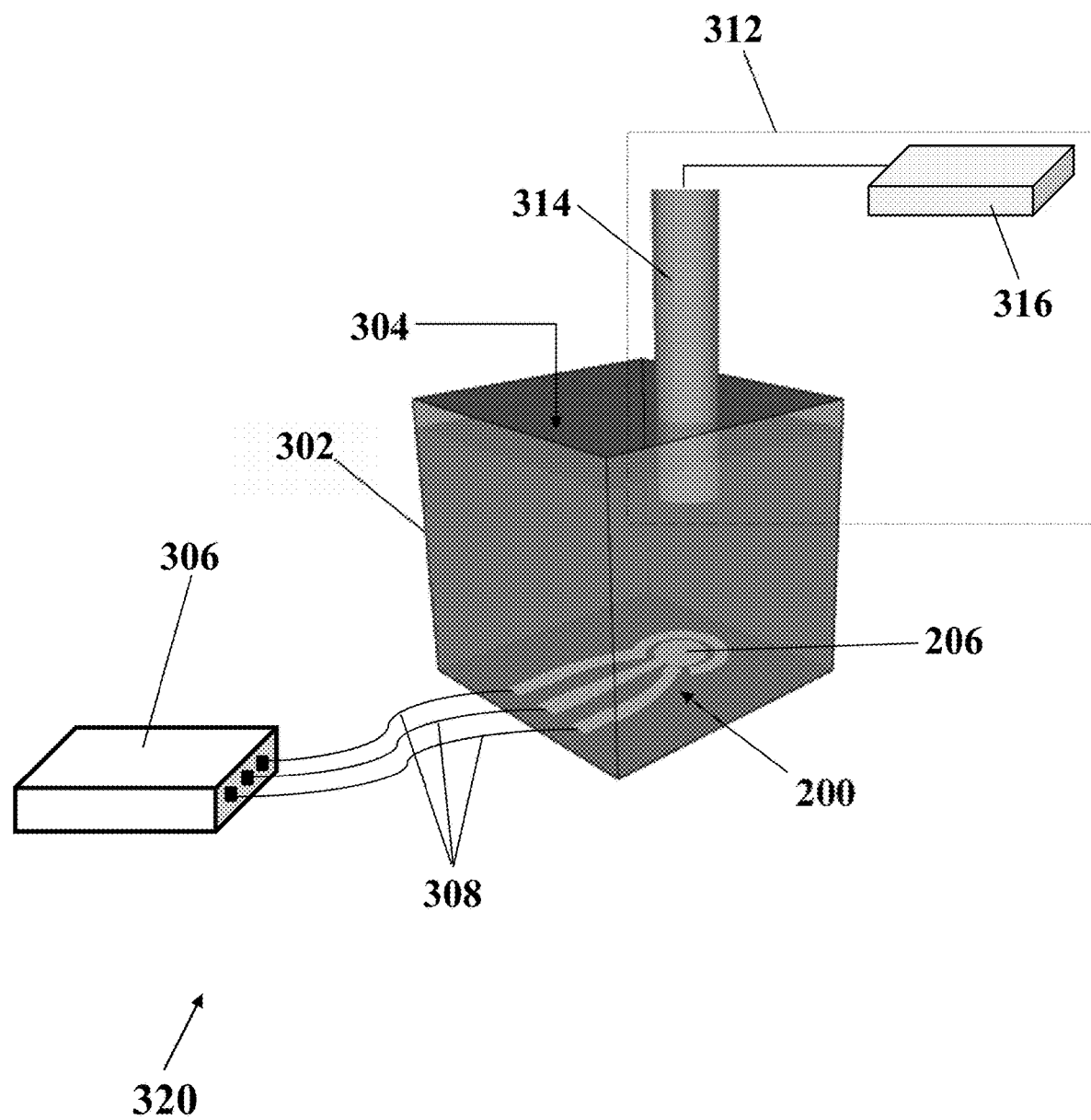
FIG. 3C illustrates a schematic view of an exemplary electrochemical-ultrasonic system, consistent with one or more exemplary embodiments of the present disclosure.

In an exemplary implementation, exemplary electrochemical system 310 (FIG. 3B) may be coupled to the ultrasonic system for conducting ultrasonically stimulating of the plurality of cultured cells on exemplary electrochemical biosensor 200; resulting in forming an electrochemical-ultrasonic system. FIG. 3C shows a schematic view of an exemplary implementation of electrochemical-ultrasonic system 320 that may be prepared by exposing exemplary electrochemical biosensor 200 to an exemplary ultrasonic system 312, consistent with one or more exemplary embodiments of the present disclosure. In an exemplary embodiment, exemplary ultrasonic system 312 may include an ultrasonic horn 314 that may be placed above exemplary electrochemical biosensor 200, for example, above exemplary working electrode 206. Additionally, exemplary ultrasonic system 312 may further include an ultrasonic generator 316 that may be connected to exemplary ultrasonic horn 314.

In an exemplary implementation, forming the plurality of stimulated cells on exemplary electrochemical biosensor 200 by ultrasonically stimulating of the plurality of cultured cells using exemplary ultrasonic system 312 may include exposing medium solution 304 containing exemplary electrochemical biosensor 200 with the plurality of cultured cells to exemplary ultrasonic system 312 and applying ultrasonic waves to medium solution 304 with a frequency range between about 10 KHz and about 100 KHz for a time duration between about 2 s and about 10 s to the plurality of cultured cells using exemplary ultrasonic system 312. Accordingly, exemplary medium solution 304 may have a third role through conducting method 100 that may include providing a medium for wave propagation of the ultrasonic stimulation in step 112 as well as a medium for cell culturing in step 104 and an electrolyte medium for electrochemical measurements in steps 110 and 114. In an exemplary embodiment, ultrasonic stimulating of the plurality of cultured cells may include applying ultrasonic waves using exemplary ultrasonic system 312 with an intensity between about 0.5 w/cm$^2$ and about 5 w/cm$^2$.

Referring to FIGS. 1A and 1B, step 114 may include measuring the second electrochemical response from exemplary electrochemical biosensor 200 with the plurality of stimulated cells using exemplary electrochemical stimulator-analyzer system 306, where the second electrochemical response may include an electrochemical response of the plurality of stimulated cells on exemplary electrochemical biosensor 200. In an exemplary implementation of step 114 and referring to FIG. 3C, the second electrochemical response may be measured form electrochemical biosensor 200 with the plurality of stimulated cells by exemplary electrochemical stimulator-analyzer system 306.

In an exemplary embodiment, measuring the second electrochemical response from exemplary electrochemical biosensor 200 with the plurality of stimulated cells may include measuring an electrochemical response via the cyclic voltammetry (CV) technique using exemplary electrochemical stimulator-analyzer system 306. The medium solution 304 may include an electrolyte solution for CV measurements as well as a culture solution in step 104 and a medium for ultrasonic stimulation in step 112. The second electrochemical response may include an electrical current, which may include an electrical current passing between exemplary working electrode 206 and counter electrode 208 in the presence of the plurality of stimulated cells on exemplary electrochemical biosensor 200.

Referring to FIGS. 1A and 1B, step 116 may include detecting presence of cancer cells responsive to a difference between the first electrochemical response and the second electrochemical response being less than a threshold. It should be noted that the difference between the first electrochemical response and the second electrochemical response may include an indicator of behavior of the plurality of the biological cells that may be cultured on exemplary electrochemical biosensor 200 before and after ultrasonic stimulation. Changes in electrochemical behavior and characteristics of different cells due to ultrasonic stimulation may be distinct from each other. Accordingly, the difference between the first electrochemical response and the second electrochemical response may be used for distinguishing distinct cells from each other, for example, cancer cells from normal (healthy) cells.

In an exemplary embodiment, cancer cells may exhibit lower difference between the first electrochemical response and the second electrochemical response due to less changes in ionic exchange states of cancer cells induced by sonoporation of cancer cells. In an exemplary embodiment, if the difference between the first electrochemical response and the second electrochemical response is less than a threshold, it may be concluded that the plurality of biological cells, which may be cultured and then stimulated through method 100, may include cancer cells. In an exemplary embodiment, the threshold may include a value of one of about 0.15 or 0.10. In an exemplary embodiment, the threshold may include a value of about 0.05 for applying the ultrasonic waves with an intensity of less than about 1 W/cm$^2$ and a duration of less than about 5 seconds to stimulate the plurality of cultured cells on exemplary electrochemical biosensor 200. In another exemplary embodiment, the threshold may include a value of about 0.15 for applying the ultrasonic waves with an intensity of more than about 1 W/cm$^2$ and a duration of less than about 5 seconds to stimulate the plurality of cultured cells on exemplary electrochemical biosensor 200.

In an exemplary implementation, the first electrochemical response may include an electrical current from exemplary electrochemical biosensor 200 before ultrasonic stimulation of the plurality of cultured cells. The second electrochemical response may include an electrical current from exemplary electrochemical biosensor 200 after ultrasonic stimulation of the plurality of cultured cells; so the second electrochemical response may include an electrical current from exemplary electrochemical biosensor 200 in the presence of the plurality of stimulated cells.

In an exemplary implementation, the first electrochemical response may include a peak current of a CV pattern measured from the plurality of cultured cells and the second electrochemical response may include a peak current of a CV pattern measured from the plurality of stimulated cells. In an exemplary embodiment, the difference between the first electrochemical response and the second electrochemical response may be defined and calculated by Eq. 1 as below:

$$\frac{\Delta I}{I} = \frac{I_{USoff} - I_{USon}}{I_{USoff}} \qquad \text{Eq. 1}$$

Where $I_{US\;off}$ may include the first electrochemical response and $I_{US\;on}$ may include the second electrochemical response. If $$\frac{\Delta I}{I}$$

is less than the threshold or $$\frac{\Delta I}{I}$$

is negligible, the plurality of stimulated cells may include cancer cells, which may mean the presence of cancer cells in the plurality of biological cells.

In an exemplary implementation, the first electrochemical response may include a first oxidation curve with a first oxidation peak and a first reduction curve with a first reduction peak. Also, the second electrochemical response may include a second oxidation curve with a second oxidation peak and a second reduction curve with a second reduction peak. In an exemplary embodiment, the difference between the first electrochemical response and the second electrochemical response may be defined and calculated by Eq. 2 as below:

$$^*P = \text{Peak to Peak } \frac{\Delta I}{I} = \frac{I_{US\,off} - I_{US\,on}}{I_{US\,off}} \qquad \text{Eq. 2}$$

Where $I_{US\,off}$, which may include the first electrochemical response, may include a first current peak of a first CV pattern measured as the first electrochemical response from the plurality of cultured cells. The first current peak may include an oxidation current peak or a reduction current peak of the first CV pattern. Also, $I_{US\,on}$, which may include the second electrochemical response, may include a second current peak of a first CV pattern measured as the second electrochemical response from the plurality of stimulated cells. The second current peak may include an oxidation current peak or a reduction current peak of the second CV pattern. If $$^*P\left(= \text{Peak to Peak } \frac{\Delta I}{I}\right)$$

is less than the threshold or $$^*P\left(= \text{Peak to Peak } \frac{\Delta I}{I}\right)$$

is negligible, the plurality of stimulated cells may include cancer cells, which may mean the presence of cancer cells in the plurality of biological cells.

In an exemplary embodiment with a reference to Eq. 2, $I_{US\,off}$ may include the first oxidation peak and $I_{US\,on}$ may include the second oxidation peak and the threshold may include a value of about 0.15. If $$^*P\left(= \text{Peak to Peak } \frac{\Delta I}{I}\right)$$

is less than the threshold (about 0.15) or $$^*P\left(= \text{Peak to Peak } \frac{\Delta I}{I}\right)$$

is negligible, the plurality of stimulated cells may include cancer cells, which may mean the presence of cancer cells in the plurality of biological cells. On the other hand, if $$^*P\left(= \text{Peak to Peak } \frac{\Delta I}{I}\right)$$

is more than the threshold (about 0.15) or $$^*P\left(= \text{Peak to Peak } \frac{\Delta I}{I}\right)$$

is negligible, the plurality of stimulated cells may include normal cells, which may an indicator of no presence of cancer cells in the plurality of biological cells.

In an exemplary embodiment with a reference to Eq. 2, $I_{US\,off}$ may include the first reduction peak and $I_{US\,on}$ may include the second reduction peak and the threshold may include a value of about 0.10. If $$^*P\left(= \text{Peak to Peak } \frac{\Delta I}{I}\right)$$

is less than the threshold (about 0.10) or $$^*P\left(= \text{Peak to Peak } \frac{\Delta I}{I}\right)$$

is negligible, the plurality of stimulated cells may include cancer cells, which may mean the presence of cancer cells in the plurality of biological cells. On the other hand, if $$^*P\left(= \text{Peak to Peak } \frac{\Delta I}{I}\right)$$

is more than the threshold (about 0.10) or $$^*P\left(= \text{Peak to Peak } \frac{\Delta I}{I}\right)$$

is negligible, the plurality of stimulated cells may include normal cells, which may an indicator of no presence of cancer cells in the plurality of biological cells.

Figure 1D:
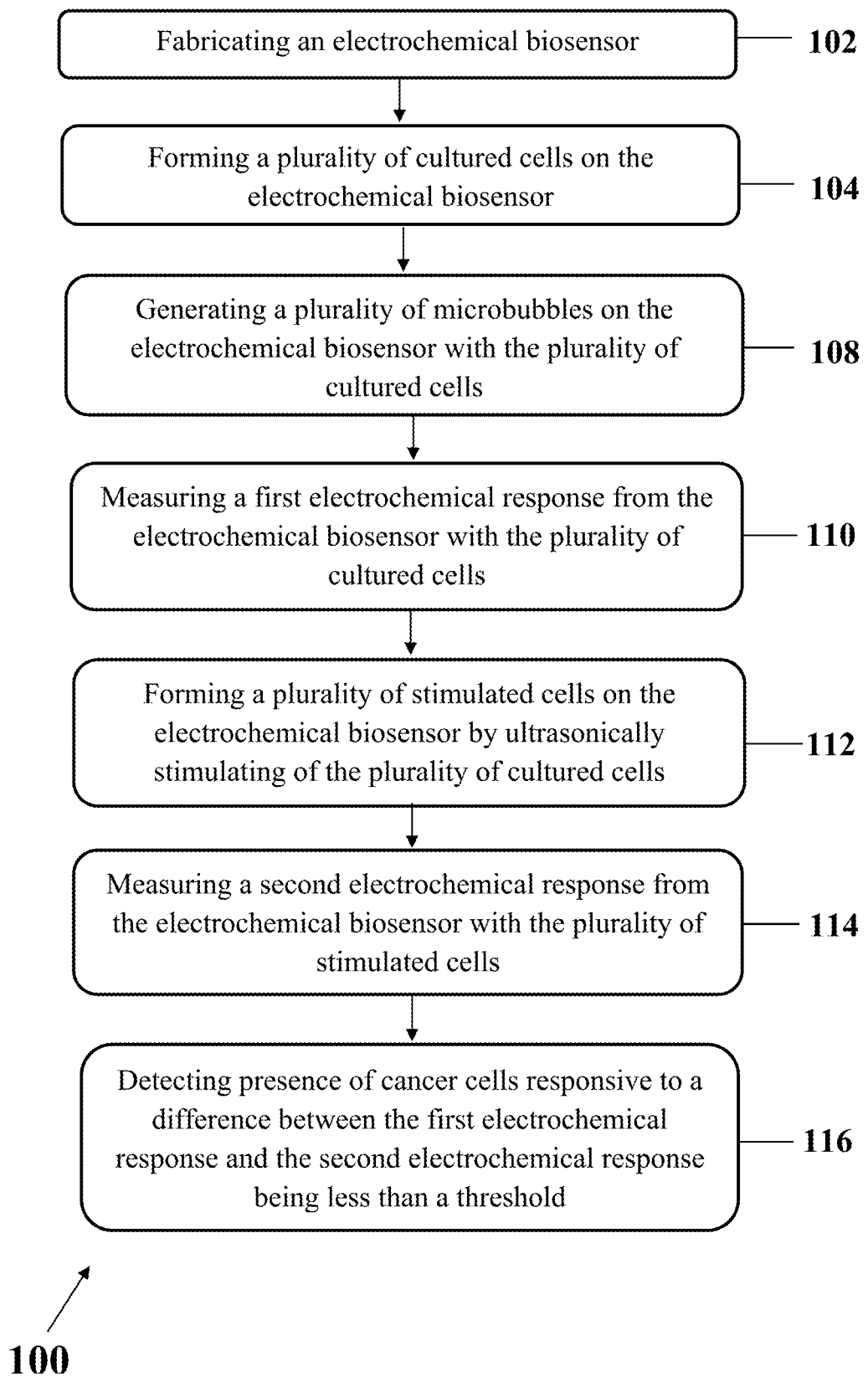
FIG. 1D illustrates a third exemplary implementation of a method for cancer diagnosis, consistent with one or more exemplary embodiments of the present disclosure.

In an exemplary implementation, method 100 may further include generating a plurality of microbubbles on the electrochemical biosensor with the plurality of cultured cells. FIG. 1D shows a third exemplary implementation of method 100 for cancer diagnosis, consistent with one or more exemplary embodiments of the present disclosure. Referring to FIG. 1D, method 100 may further include generating a plurality of microbubbles on the electrochemical biosensor with the plurality of cultured cells (step 108). The plurality of microbubbles may be generated on the electrochemical biosensor with the plurality of cultured cells in order to improve and intensify the sonoporation of cultured cells during step 112.

In an exemplary implementation, step 108 may include generating the plurality of microbubbles on exemplary electrochemical biosensor 200 with the plurality of cultured cells may include electrolysis of exemplary medium solution 304 by applying an instantaneous electrical potential to exemplary electrochemical biosensor 200 via a cyclic voltammetry technique using exemplary electrochemical stimulator-analyzer system 306. So the plurality of microbubbles may be generated in-situ without any need to insert microbubbles onto exemplary electrochemical-ultrasonic system 320. So another role for exemplary medium solution 304 may be for use of exemplary medium solution 304 for generation of the plurality of microbubbles.

In an exemplary embodiment, generating the plurality of microbubbles on exemplary electrochemical biosensor 200 with the plurality of cultured cells may include applying a DC signal with a voltage between about −2 V and about −0.5 V, for example, about −1.7 V, for a time duration less than about 1 seconds on exemplary electrochemical biosensor 200 with the plurality of cultured cells using exemplary electrochemical stimulator-analyzer system 306, for example, a potentiostat device.

In an exemplary embodiment, by applying generating the plurality of microbubbles on exemplary electrochemical biosensor 200 with the plurality of cultured cells (step 108) in exemplary method 100, forming the plurality of stimulated cells on the electrochemical biosensor by ultrasonic stimulation of the plurality of cultured cells using the ultrasonic system (step 112) may include ultrasonic stimulating of the plurality of cultured cells responsive to applying ultrasonic waves to the plurality of cultured cells exemplary electrochemical biosensor 200 in exemplary medium solution 304, and inducing an acoustic cavitation in the plurality of cultured cells by the plurality of microbubbles responsive to applying ultrasonic waves to the plurality of microbubbles on exemplary electrochemical biosensor 200 in exemplary medium solution 304.

Figure 4:
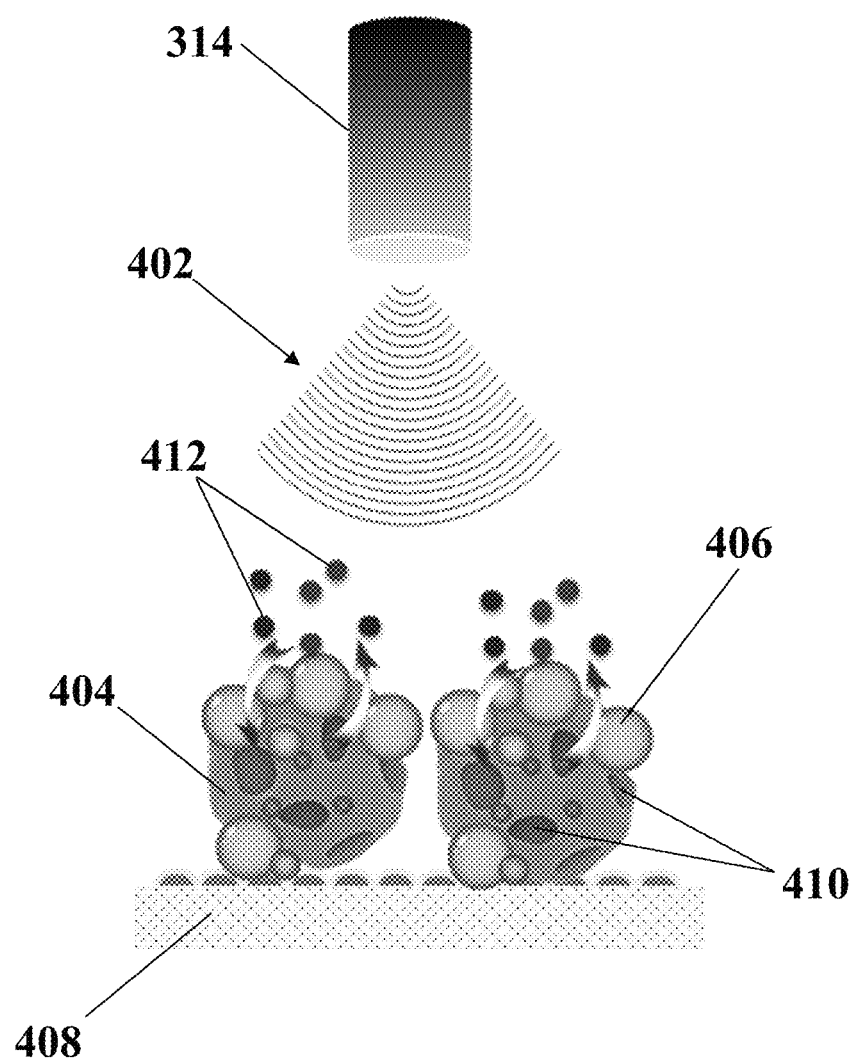
FIG. 4 illustrates a schematic view of ultrasonic stimulation of the plurality of cultured cells in the presence of the plurality of microbubbles on exemplary electrochemical biosensor, consistent with one or more exemplary embodiments of the present disclosure.

FIG. 4 shows a schematic view of ultrasonic stimulation of the plurality of cultured cells in the presence of the plurality of microbubbles on exemplary electrochemical biosensor 200, consistent with one or more exemplary embodiments of the present disclosure. Referring to FIG. 4, ultrasonic waves 402 may be applied using exemplary ultrasonic horn 314 to exemplary plurality of cultured cells and exemplary plurality of microbubbles 406 on exemplary portion 408 of exemplary working electrode 206. Ultrasonic waves may cause stimulation or sonoporation of exemplary plurality of cultured cells; thereby, forming exemplary plurality of stimulated cells 404 with exemplary sonopores 410. Additionally, ultrasonic waves may cause stimulation of exemplary plurality of microbubbles 406 that may induce acoustic cavitation in exemplary plurality of stimulated cells 404-resulting in enhancing the sonoporation of exemplary plurality of stimulated cells 404. Therefore, the variations of the ion exchanges of exemplary ions 412 between exemplary plurality of stimulated cells 404 and exemplary medium solution 304 may be intensified, which may be monitored by electrochemical responses measured by exemplary electrochemical stimulator-analyzer system 306.

EXAMPLE 1

Fabrication and Characterization of the Electrochemical Biosensor

In this example, an exemplary electrochemical biosensor including integrated three electrodes was fabricated. To fabricate the electrochemical biosensor, Poly(methyl methacrylate) (PMMA/plexiglass®) was used as the substrate. PMMA was roughened by Reactive Ion Etching (RIE) equipment in which the region of working electrode (WE) was processed and roughened by $SF_6$, $H_2$ and $O_2$ gases with exemplary flows of about 100 sccm for $SF_6$, 80 sccm for $H_2$ and 85 sccm for $O_2$ in the presence of RF Plasma at about 13.56 MHz to form nanoroughened surface. RF Plasma causes the ionization of $SF_6$ which plays the key role as etching radical. The plasma power was about 190 W and the period of the bombarding sub-cycle was about 50 s. The combination of $H_2/O_2$ and $SF_6$ during the settling step resulted in the creation of a protecting layer over the side walls of the formed nanohills in each sub-cycle. The sequential treatment of the PMMA by SF6 followed by the combination of $H_2/O_2$ and $SF_6$ as passivation layer in the presence of RF plasma, roughens the surface.

Figure 5A:
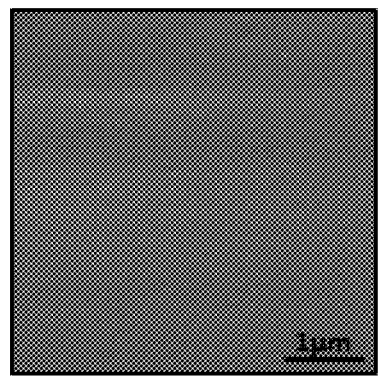
FIG. 5A illustrates a field emission scanning electron microscopy (FESEM) image of exemplary pristine PMMA surface, consistent with one or more exemplary embodiments of the present disclosure.
Figure 5B:
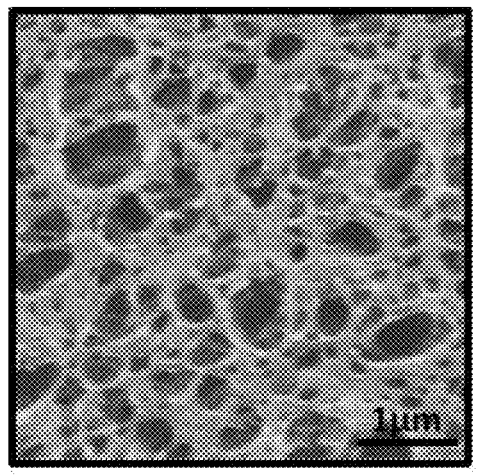
FIG. 5B illustrates a FESEM image of exemplary nanoroughened PMMA surface, consistent with one or more exemplary embodiments of the present disclosure.

FIGS. 5A and 5B show field emission scanning electron microscopy (FESEM) images of exemplary pristine PMMA surface (FIG. 5A) and exemplary nanoroughened PMMA surface (FIG. 5B), consistent with one or more exemplary embodiments of the present disclosure. The exemplary nanoroughened PMMA surface (FIG. 5B) shows formation of nanoroughening features in comparison with the initial pristine PMMA surface (FIG. 5A).

Figure 5C:
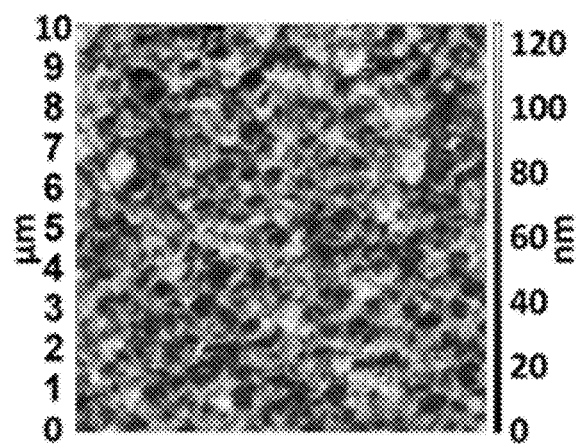
FIG. 5C illustrates an atomic force microscopy (AFM) profile of exemplary nanoroughened PMMA surface, consistent with one or more exemplary embodiments of the present disclosure.

FIG. 5C shows atomic force microscopy (AFM) profile of exemplary nanoroughened PMMA surface, consistent with one or more exemplary embodiments of the present disclosure. Surface roughness and topography of the both pristine and nanoroughened PMMA were collected by atomic force microscopy (AFM, NT-MDT Solver Next). About 100 μm$^2$ of the surface was scanned for three times in different sections to evaluate the differences in roughness between pristine PMMA and the processed PMMA. Using this method, nanoroughened pattern was obtained with a roughness of about 70 nm as shown in AFM profile of FIG. 5C.

After surface treatment of the PMMA and forming of the nanoroughened surface, the PMMA nanoroughened surface was coated with a gold layer with about 30 nm thickness using RF sputtering system. To promote the adherence of the gold to PMMA, prior to this step, a thin layer of Titanium with about 5 nm thickness was sputtered on PMMA substrate. So an Au/Ti bilayer (about 30/5 nm) was deposited on the PMMA nanoroughened surface. Finally, a desired pattern of the biosensor was projected onto the Ti/Au coated nanoroughened PMMA substrate using standard photolithography technique.

Figure 6:
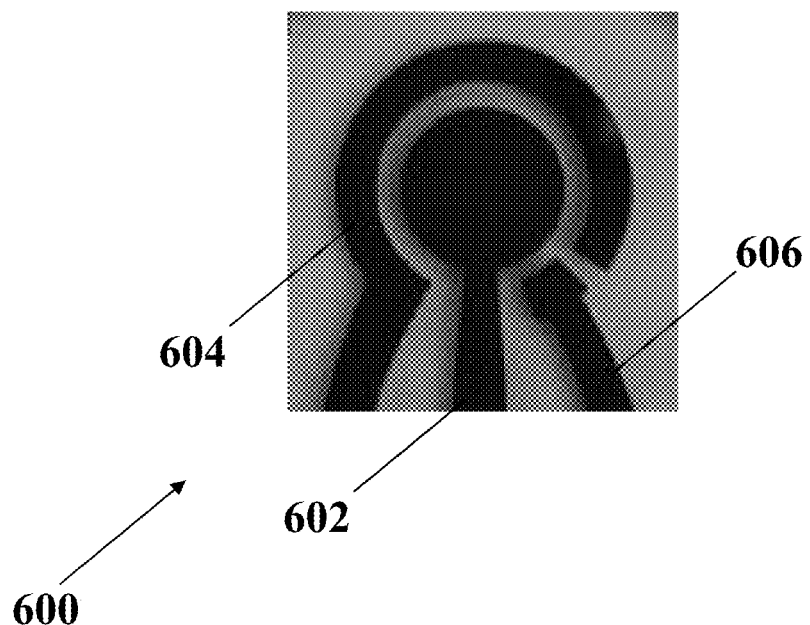
FIG. 6 illustrates an optical image of exemplary fabricated electrochemical biosensor with three-integrated circular-patterned electrodes, consistent with one or more exemplary embodiments of the present disclosure.

FIG. 6 shows an optical image of exemplary fabricated electrochemical biosensor 600 with three-integrated circular-patterned electrodes as an example of exemplary electrochemical biosensor 200, consistent with one or more exemplary embodiments of the present disclosure. Exemplary fabricated electrochemical biosensor 600 includes a circular working electrode 602 with the diameter of about 5 mm surrounded by a ring shaped counter electrode 604 with a thickness of about 1 mm and a reference electrode 606. The distance between counter electrode 604/reference electrode 606 and working electrode 602 is about 1 mm.

EXAMPLE 2

Preparing the Electrochemical-Ultrasound System

In this example, an exemplary system as an example of exemplary electrochemical-ultrasonic system 320 shown in FIG. 3C was prepared for ultrasonic stimulation of exemplary biological cells and electrochemical detection of presence of cancer cells in exemplary biological cells. The cells were cultured on the working electrode of exemplary fabricated electrochemical biosensor 600 of EXAMPLE 1. For exemplary tests, MCF-10A (human normal breast cell line) and MCF-7 (human noninvasive breast cancer cell line) were cultured in Rose well Park Memorial Institute medium (RPMI), supplemented with about 10% FBS and about 1% penicillin/streptomycin antibiotics. Cells were maintained in an incubator under standard cell culture conditions (37° C., 5% CO2) and the medium was changed every two days. Then exemplary fabricated electrochemical biosensor 600 was placed at the bottom of an exemplary chamber (or a box) with the height of about 5 cm. Then, the chamber was filled with cell culture solution, including RPMI containing about 10% fetal bovine serum (FBS) and about 1% antibiotics, which may serve as an electrolyte for CV measurement as well as a medium for wave propagation of the ultrasonic stimulation. An exemplary ultrasonic horn with diameter of about 12 mm was placed about 4 cm above the working electrode. Frequency of the ultrasound generator was preset at about 20 KHz and about 2 s was selected for time duration of stimulation. The US intensity was set to about 0.9 w/cm² and about 1.8 w/cm².

EXAMPLE 3

Characterization of the Electrochemical Biosensor and the Cell Culture Medium In this example, $K_3[Fe(CN)_6]$ standard redox probe was used to investigate the electrochemical response of exemplary fabricated electrochemical biosensor 600. Exemplary fabricated electrochemical biosensor 600 was analyzed by cyclic voltammetry by cycling the potential of the sensor between −600 mV to 600 mV at a scan rate of 100 mV/s using 5 mM of standard redox probe, $K_3[Fe(CN)_6]$.

Figure 7A:
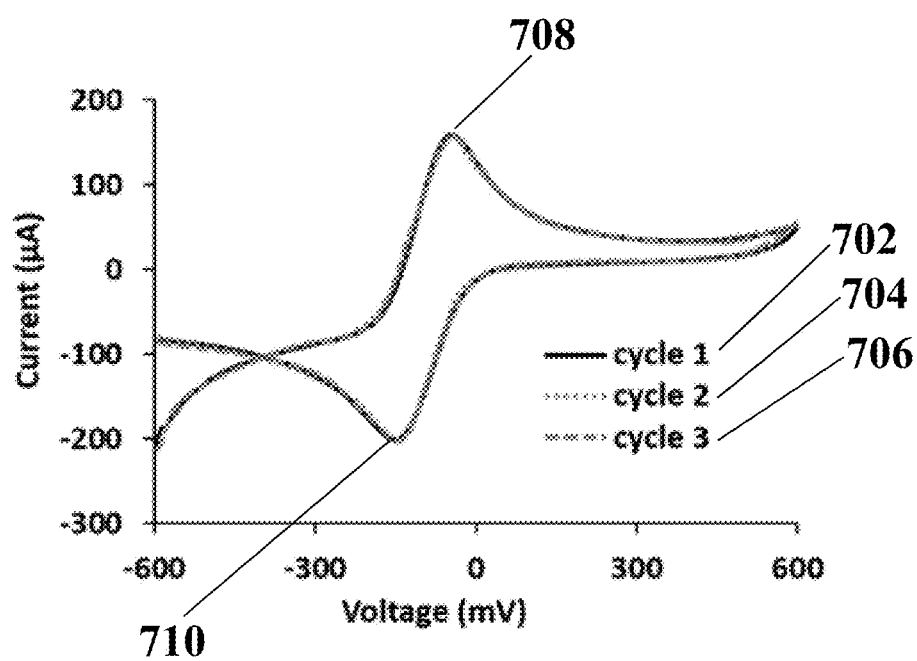
FIG. 7A illustrates three consecutive cyclic voltammetry (CV) responses of exemplary fabricated electrochemical biosensor to Ferricyanide as a standard ionic solution, consistent with one or more exemplary embodiments of the present disclosure.

FIG. 7A shows three consecutive CV responses 702 for cycle 1, 704 for cycle 2, and 706 for cycle 3 of exemplary fabricated electrochemical biosensor 600 to Ferricyanide as a standard ionic solution, consistent with one or more exemplary embodiments of the present disclosure. Cycling the potential of the sensor with scan rate of 100 mV/s indicated the presence of high intensity oxidation/reduction peaks 708 and 710, which may corroborate well electrochemical response of the sensor. The obtained result shows the presence of both anodic and cathodic current with high intensity representing well electrochemical behavior of exemplary fabricated electrochemical biosensor 600 and great charge transfer of the nanoroughened PMMA. In addition, three consecutive potential cycles (cycle 1, cycle 2, and cycle 3) of the standard solution are coincided on each other which may corroborate the sensor reproducibility.

As the cells must be kept in cell culture medium to keep alive, the cyclic voltammetry response of the cell culture medium was measured. This response would be the background response of the CV voltammograms in the presence of the cells. RPMI1640 containing about 10% FBS and about 1% antibiotics was used for all tests herein. Firstly the CV response was investigated in the presence of cells media solution as the environment existed in all of the measurements.

Figure 7B:
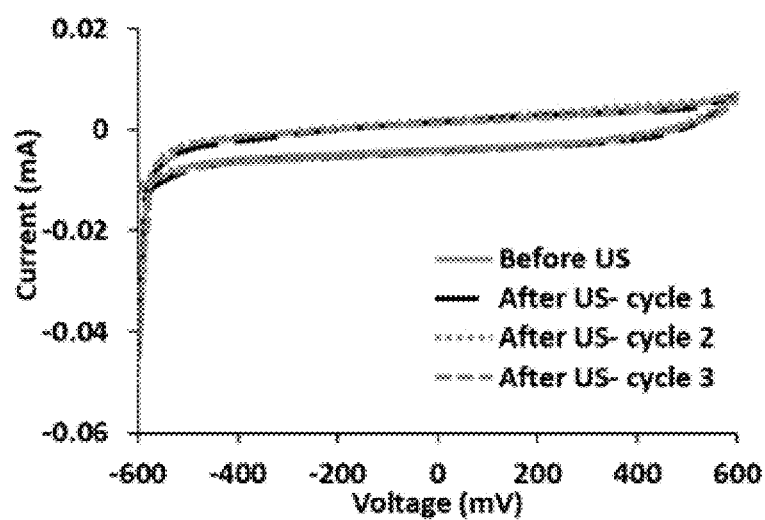
FIG. 7B illustrates cyclic voltammogram of cell culture medium before ultrasonic stimulation and three cycles after ultrasonic stimulation, consistent with one or more exemplary embodiments of the present disclosure.

FIG. 7B shows cyclic voltammogram of cell culture medium before ultrasonic stimulation and three cycles after ultrasonic stimulation, consistent with one or more exemplary embodiments of the present disclosure. As presented in FIG. 7B, no oxidation/reduction peaks were detected for RPMI in the CV response of exemplary fabricated biosensor 600. Moreover, coincidence of three CV responses after US to nonstimulated cell culture medium indicates no destructive effect of US on sole culture medium.

Figure 7C:
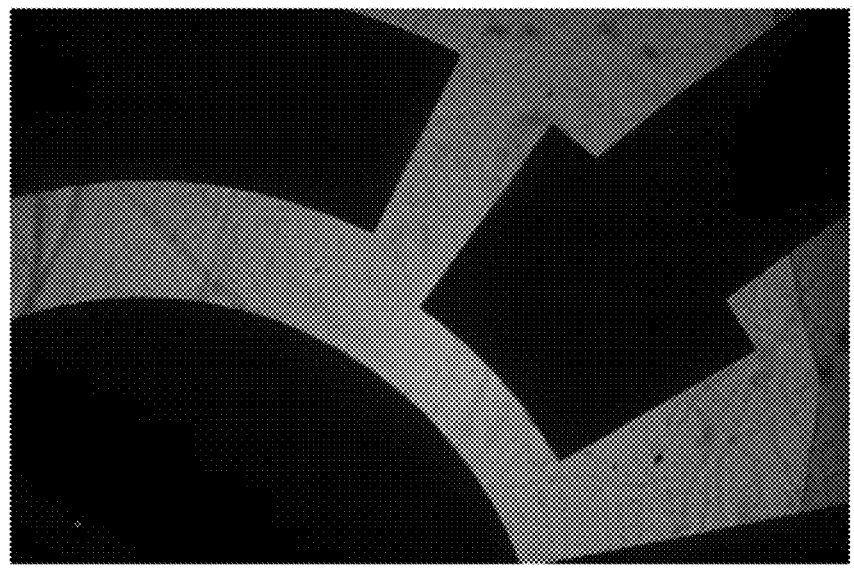
FIG. 7C illustrates an optical image of exemplary electrochemical biosensor before ultrasonic stimulation, consistent with one or more exemplary embodiments of the present disclosure.
Figure 7D:
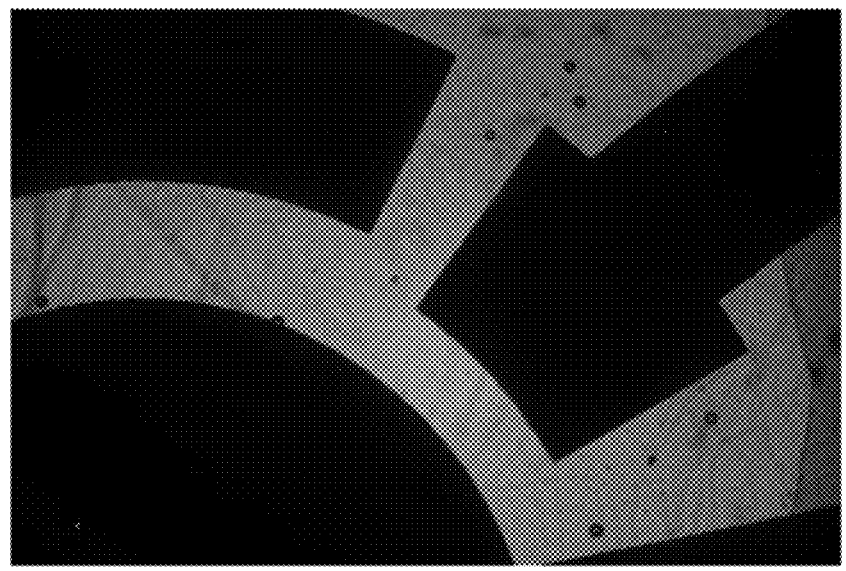
FIG. 7D illustrates an optical image of exemplary electrochemical biosensor after ultrasonic stimulation, consistent with one or more exemplary embodiments of the present disclosure.

FIGS. 7C and 7D show optical images of exemplary fabricated biosensor 600 before and after ultrasonic stimulation, consistent with one or more exemplary embodiments of the present disclosure. Comparing these two figures, no changes is seen in the shape and morphology of the electrodes after three times of ultrasonic stimulation.

EXAMPLE 4

Microbubbles Generation

In this example, exemplary microbubbles were generated on the surface of exemplary fabricated electrochemical biosensor 600 in EXAMPLE 1. Microbubbles may be generated to facilitate the sonoporation of exemplary cells attached onto the working electrode of exemplary fabricated electrochemical biosensor 600. In this regards, an instantaneous potential of about −1.7 V via a cyclic voltammetry process was applied to the three integrated electrodes of exemplary fabricated electrochemical biosensor 600 using a Potentio Galvanostat. Rapid potential stimulation may give a rise to the electrolysis of the cell culture medium solution, which exemplary fabricated electrochemical biosensor 600 placed in and subsequently microbubbles on the surface of the working electrode of exemplary fabricated electrochemical biosensor 600 may be generated.

Figure 8A:
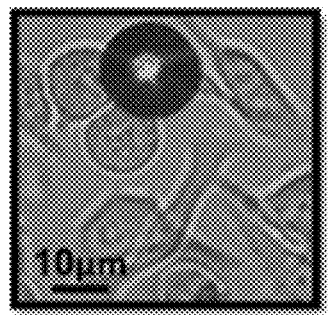
FIG. 8A illustrates a microscopic image of an exemplary produced microbubble on the working electrode by cyclic voltammetry at about −1.7 V electrical potentials, consistent with one or more exemplary embodiments of the present disclosure.
Figure 8B:
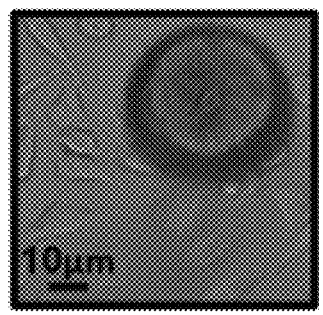
FIG. 8B illustrates a microscopic image of an exemplary produced microbubble on the working electrode by cyclic voltammetry at about −2 V electrical potentials, consistent with one or more exemplary embodiments of the present disclosure.
Figure 8C:
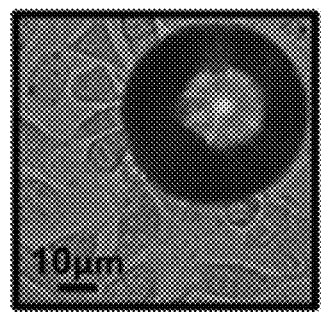
FIG. 8C illustrates a microscopic image of an exemplary produced microbubble on the working electrode by cyclic voltammetry at about −2.2 V electrical potentials, consistent with one or more exemplary embodiments of the present disclosure.

FIGS. 8A-8C show microscopic images of exemplary produced microbubbles on the surface of the cells attached on exemplary working electrode 602 by cyclic voltammetry in different electrical potentials, consistent with one or more exemplary embodiments of the present disclosure. It was found that the electrolysis of the solution for microbubble generation occurred at minimum potential of about −1.7 V (FIG. 8A), so before recording the CV response of the cells to ultrasonic stimulation microbubbles were produced to enhance sonoporation. Higher voltages also may be applied for microbubble production but as the voltage increases, for example, to about −2 V (FIG. 8B) and about −2.2 V (FIG. 8C), the size of the produced microbubbles may also amplified. This size increasing may cause the destructive burst of the microbubbles which may detach some of the cells from the working electrode and perturb the electrochemical responses. Therefore, a potential of about −1.7 V was used for further sonoporation processes, which may produce the minimum size of the microbubbles while improving the sonoporation.

Figure 8D:
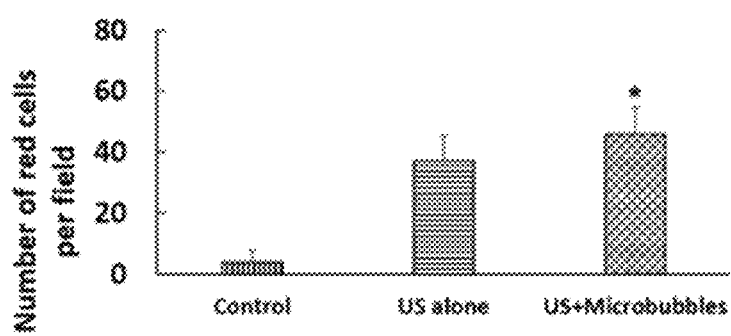
FIG. 8D shows number of sonoporated cells per field formed after ultrasonic stimulation (US) in the presence and absence of microbubbles, consistent with one or more exemplary embodiments of the present disclosure.

Moreover, image analysis was carried out to quantify the efficiency of the sonoporation based on PI staining. FIG. 8D shows number of sonoporated cells per field formed after ultrasonic stimulation (US) in the presence and absence of microbubbles, consistent with one or more exemplary embodiments of the present disclosure. The image analysis results shown in FIG. 8D reveals an increase in the number of sonoporated cells in the presence of microbubbles compared to the US-alone state.

EXAMPLE 5

Figure 9A:
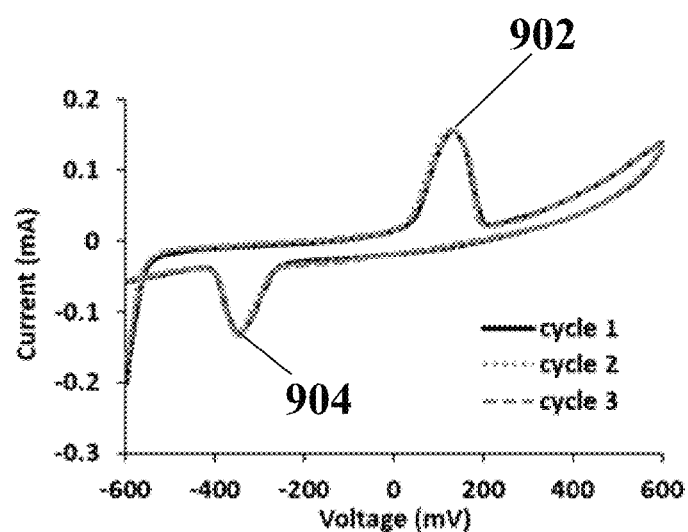
FIG. 9A illustrates effect of successive cyclic voltammetry on CV diagram of MCF-7 cells in the absence of US, consistent with one or more exemplary embodiments of the present disclosure.

Characterization of CV Responses Measurements of Cells Using the Electrochemical Biosensor In this example, the electrochemical response of MCF-7 cells was measured. In this regard, the CV of non-stimulated MCF-7s covered on exemplary working electrode 602 for three successive cycles was investigated in the absence of ultrasound stimulation. FIG. 9A shows effect of successive cyclic voltammetry on CV diagram of MCF-7 cells in the absence of US, consistent with one or more exemplary embodiments of the present disclosure. As seen in FIG. 9A, when the cells are cultured on the exemplary working electrode 602, both oxidation peak 902 and reduction peak 904 emerged. Since cell culture medium presented neither cathodic nor anodic peaks, therefore the electrochemical peak arisen in the presence of the cells could be contributed to the cell electrochemical metabolism. In addition, three consecutive cyclic voltammetry indicates no change in the current peaks and all cycles are coincident demonstrating no effect of consecutive CV measurement on peak change.

Figure 9B:
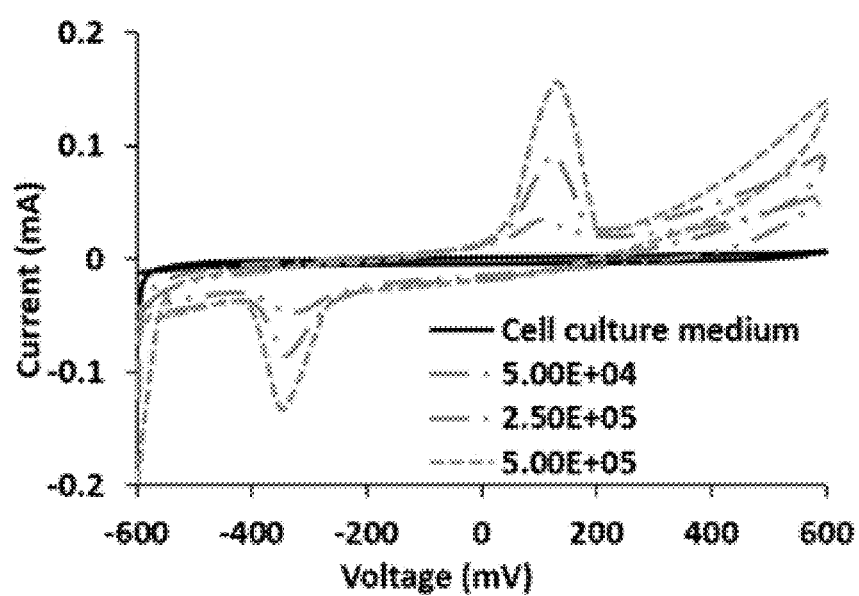
FIG. 9B illustrates cyclic voltammogram of MCF-7 cells with different numbers cultured on working electrode, consistent with one or more exemplary embodiments of the present disclosure.

Moreover, the effect of cell density on the CV responses of the biosensor was investigated. FIG. 9B shows cyclic voltammogram of MCF-7 cells with different numbers cultured on working electrode, consistent with one or more exemplary embodiments of the present disclosure. A positive relationship may be seen between the number of attached cells and the peak currents in either normal or cancer cells. This might be due to the increased number of ions exchanged by added cells.

Figure 9C:
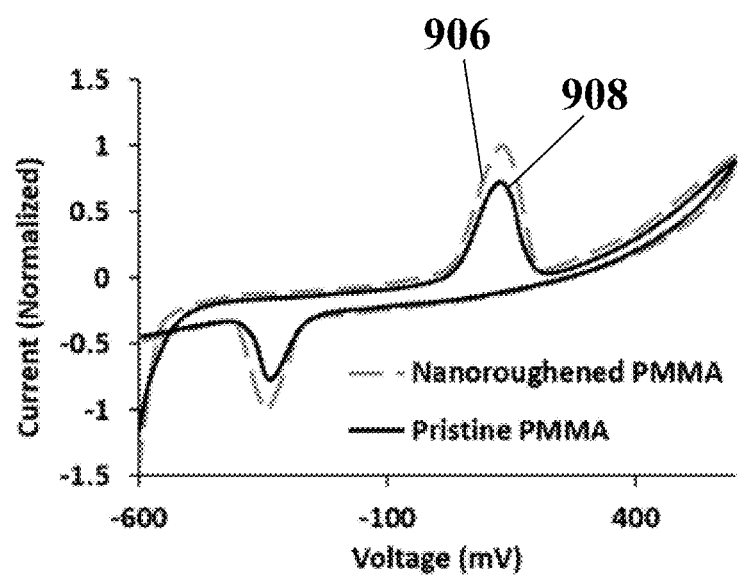
FIG. 9C illustrates the effect of electrode nanoroughening on the electrochemical peaks of the MCF-7 cells, consistent with one or more exemplary embodiments of the present disclosure.

FIG. 9C shows the effect of electrode nanoroughening on the electrochemical responses of the MCF-7 cells (Both oxidation and reduction curves were normalized to the nanoroughened PMMA peak response in all tests carried out utilizing exemplary fabricated electrochemical biosensor 600), consistent with one or more exemplary embodiments of the present disclosure. The nanoroughened PMMA substrate of exemplary fabricated electrochemical biosensor 600 may provide an extensive area for interaction between exchanging ions and the electrodes. Moreover, nanoroughening may improve the cell attachment as an accepted evidence. Therefore, as shown in FIG. 9C, the cells seeded on the nanoroughened working electrode 602 indicated a stronger electrochemical response (curve 906) compared to a sensor with pristine PMMA (curve 908).

EXAMPLE 6

CV Responses of the Healthy and Cancerous Cells to US

In this example, the electrochemical response of the breast normal (healthy) cells MCF-10A and breast cancer cells MCF-7 to ultrasonic stimulation was measured. Cyclic voltammetry measurements were carried out in exemplary electrochemical-ultrasonic system 320 that was prepared in EXAMPLE 2. Before ultrasonic stimulation and to measure the initial electrochemical response of cultured cell lines on exemplary working electrode 602, cyclic voltammetry was performed in a voltage range of about −600 mV to about 600 mV with scan rate of about 100 mV/s. For all CV measurements, these limits were kept constant. After recording the initial CV response of the nonstimulated cells, the ultrasonic stimulation (US) was applied and again the CV response of the cells was measured. Before launching the experiment, microbubbles were formed by applying an instantaneous potential of about −1.7 V using to enhance sonoporation.

Ultrasound induced cyclic voltammogram of the cells were normalized to the oxidation/reduction peak response of the nonstimulated cells and then, $$\frac{\Delta I}{I}$$

was calculated as represented by Eq. 1 hereinabove.

Figure 10A:
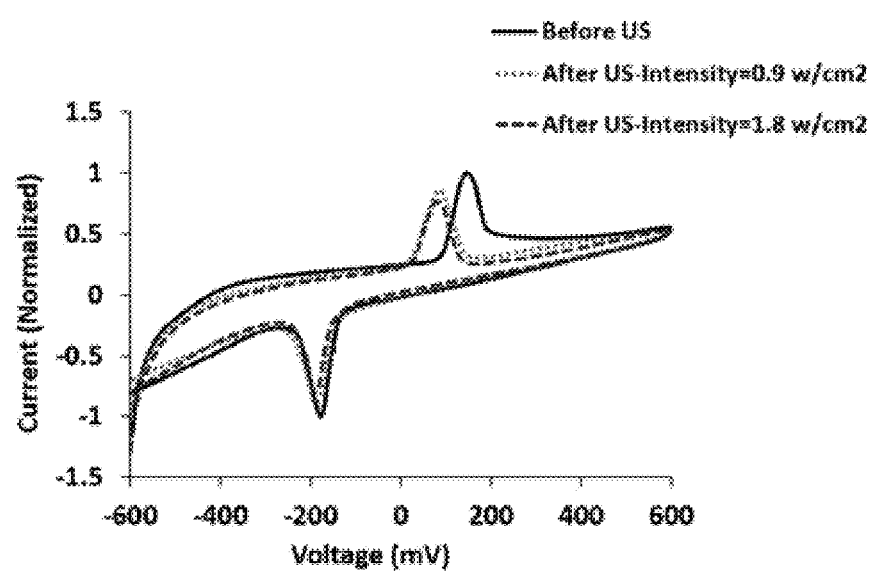
FIG. 10A illustrates the electrochemical responses of healthy cells MCF-10A before and after ultrasonic stimulation, consistent with one or more exemplary embodiments of the present disclosure.
Figure 10B:
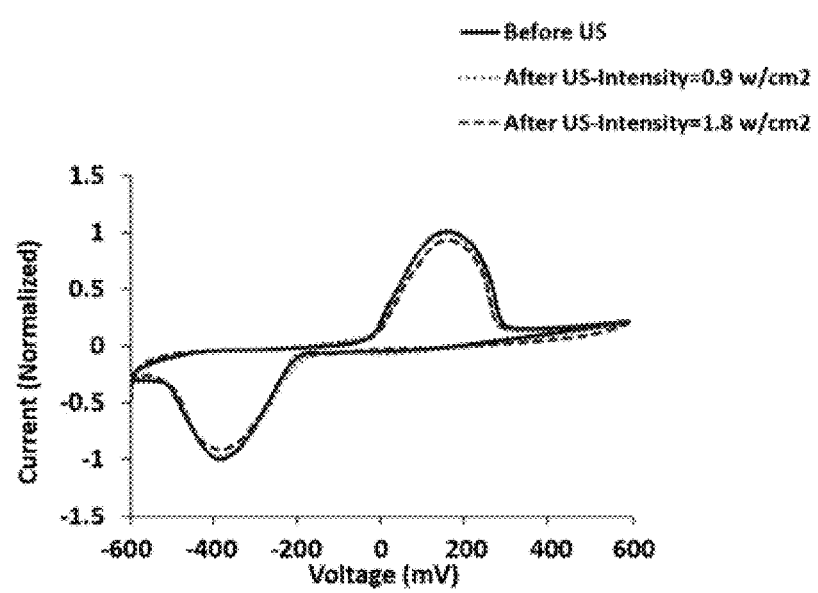
FIG. 10B illustrates the electrochemical responses of cancer cells MCF-7 before and after ultrasonic stimulation, consistent with one or more exemplary embodiments of the present disclosure.
Figure 10C:
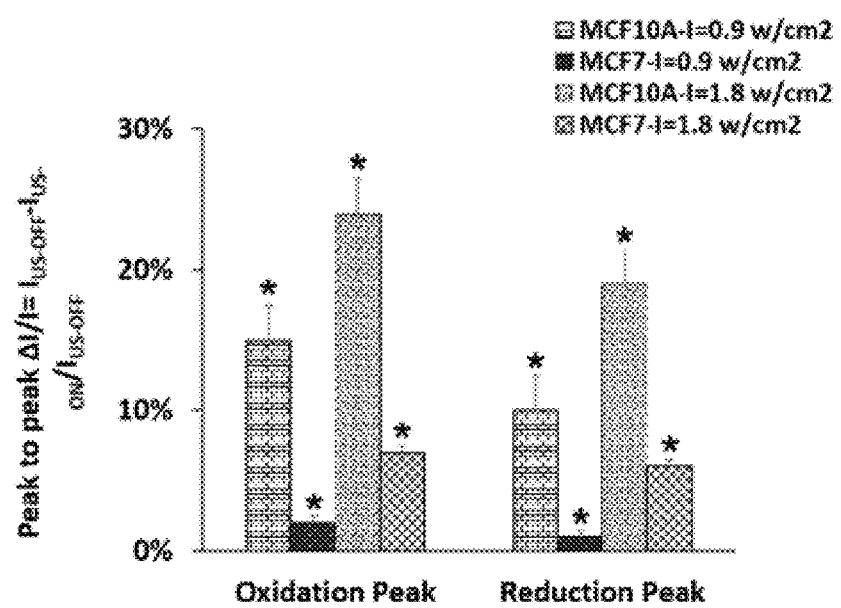
FIG. 10C illustrates ratio of peak intensity deviation of MCF-10A and MCF-7 cell lines after ultrasonic stimulation with respect to their nonstimulated state (Peak to Peak $\Delta I/I=(I\_(US\ off)-I\_(US\ on))/I\_(US\ off)$), consistent with one or more exemplary embodiments of the present disclosure.

FIGS. 10A and 10B show electrochemical responses of healthy MCF-10A cells (FIG. 10A) and cancer cells MCF-7 (FIG. 10B) before ultrasonic stimulation and after ultrasonic stimulation with two different intensities for ultrasonic waves, consistent with one or more exemplary embodiments of the present disclosure. Both oxidation and reduction curves were normalized to their US off peak response. FIG. 10C shows ratio of peak intensity deviation of MCF-10A and MCF-7 cell lines after ultrasonic stimulation with respect to their nonstimulated state $$\left(\text{Peak to Peak } \frac{\Delta I}{I} = \frac{I_{US\,off} - I_{US\,on}}{I_{US\,off}}\right),$$

where *p<0.05 compared with 'before US' state, consistent with one or more exemplary embodiments of the present disclosure. Moreover, Table 1 represents the effect of ultrasonic intensity on the peak current of the sensor in MCF-10A and MCF-7 cells. Table 1 indicates the supportive effect of different parameters of ultrasonic stimulation on the peak current.

TABLE 1

Comparative effect of US parameters on the electrochemical peak current between breast normal and cancer cells.

| Cell type | | US parameters | | | | | | ~$\frac{\Delta I}{I}\% = \frac{I_{US\,off} - I_{US\,on}}{I_{US\,off}}$ | |
|---|---|---|---|---|---|---|---|---|---|
| | | | | | | | | Oxidation | Reduction |
| MCF-10A | Intensity | $I = 0.9 \frac{w}{cm^2}$ | Cell number | $N = 5 \times 10^5$ | US duration | $t = 2\,s$ | | 15% | 10% |
| | | $I = 1.8 \frac{w}{cm^2}$ | | $N = 5 \times 10^5$ | | $t = 2\,s$ | | 24% | 19% |
| | | $I = 1.8 \frac{w}{cm^2}$ | | $N = 5 \times 10^5$ | | $t = 3\,s$ | | 37% | 30% |
| MCF-7 | Intensity | $I = 0.9 \frac{w}{cm^2}$ | Cell number | $N = 5 \times 10^5$ | US duration | $t = 2\,s$ | | 2% | 1% |
| | | $I = 1.8 \frac{w}{cm^2}$ | | $N = 5 \times 10^5$ | | $t = 2\,s$ | | 7% | 6% |
| | | $I = 1.8 \frac{w}{cm^2}$ | | $N = 5 \times 10^5$ | | $t = 3\,s$ | | 12% | 8% |

Referring to FIGS. 10A-10C and Table 1, when the intensity of US was about 0.9 w/cm², about 15% changes in oxidation and about 10% in reduction peaks of MCF-10A cells was observed with respect to non-stimulated state (FIGS. 10A and 10C). The result of similar experiment (I=about 0.9 w/cm²) on cancerous MCF-7 cells (FIGS. 10B and 10C) showed no significant changes in the post US peaks which might refer to reduced ionic exchanging abilities between the cancer cells and media (FIG. 10C). Rising the intensity of the US to about 1.8 w/cm² increased the discrepancy between oxidation/reduction peaks of the stimulated and nonstimulated cells (FIG. 10C and Table 1). Moreover, increasing the US duration to about 3 s brought about extensive changes in peak currents of the stimulated cells (Table 1). These results exhibited a correlation with increased sonopores in US stimulated cells which improve ion exchanges between the cells and the medium solution. Different electrochemical responses between sonoporated normal and cancerous breast cell lines, might relate to their different ionic exchange states. It mean that the breast cancer cell exhibited lower changes in electrochemical response after being sonoporated.

Figure 11A:
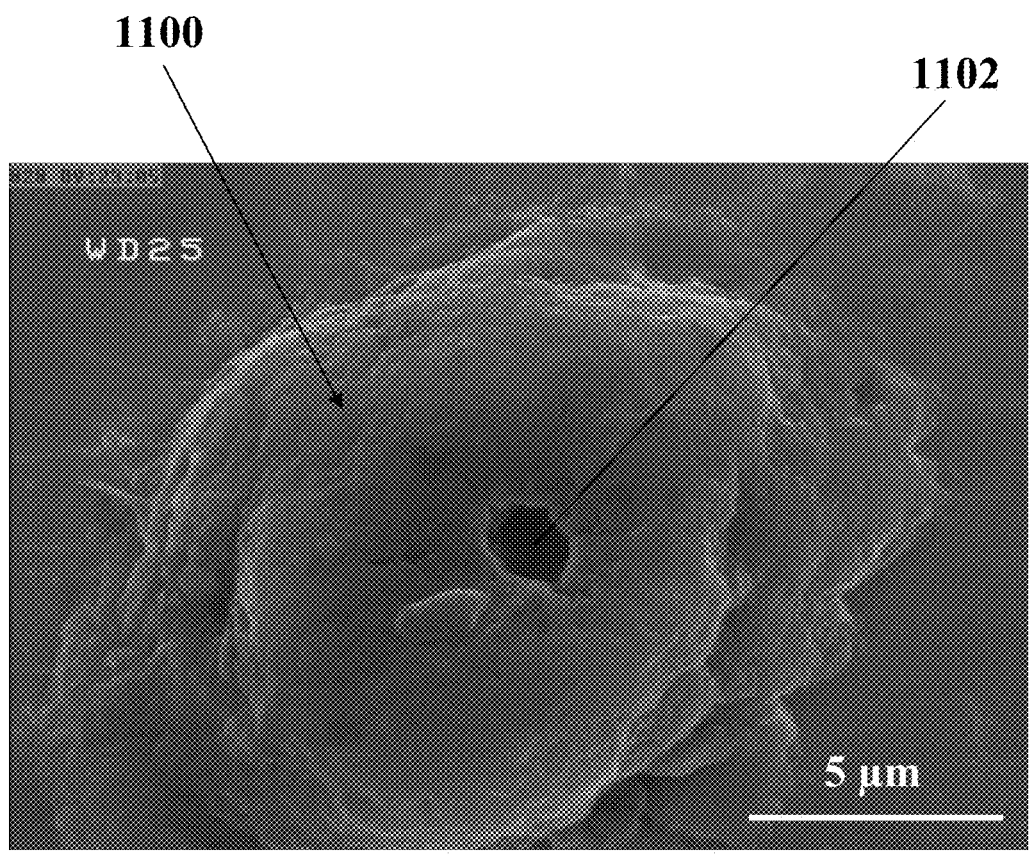
FIG. 11A illustrates a FESEM image of exemplary MCF-10A normal cell after US, consistent with one or more exemplary embodiments of the present disclosure.
Figure 11B:
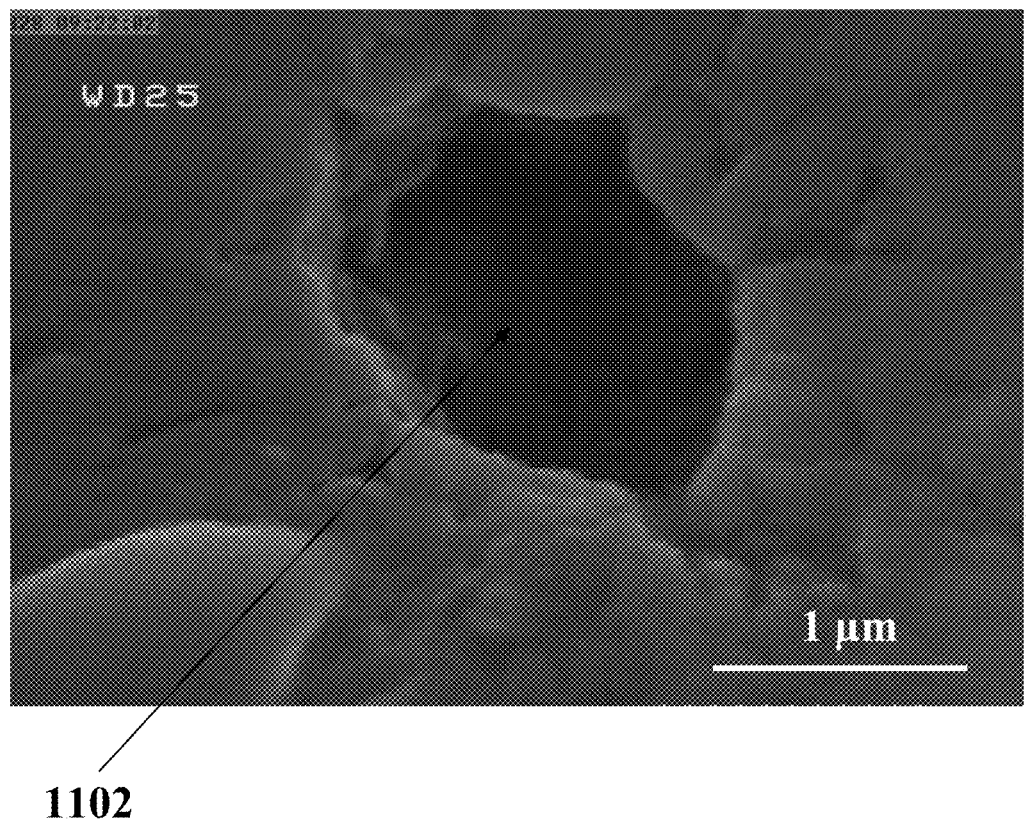
FIG. 11B illustrates a magnified FESEM image of exemplary sonopore formed in exemplary MCF-10A normal cell after US, consistent with one or more exemplary embodiments of the present disclosure.
Figure 11C:
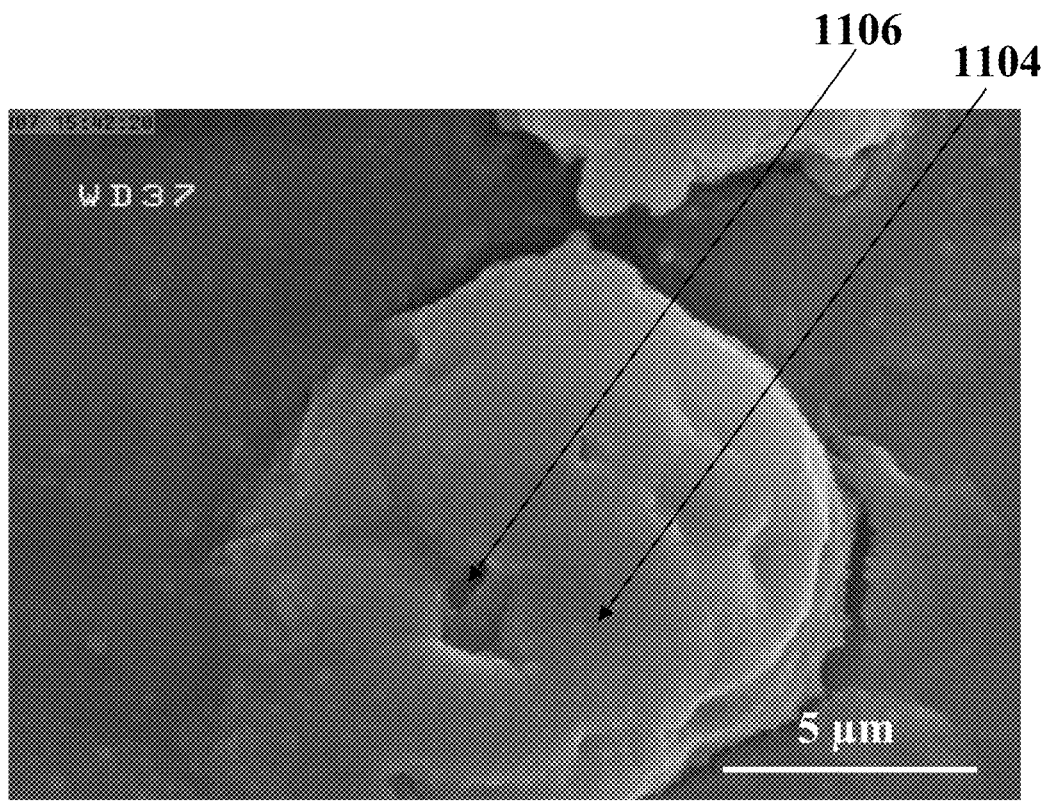
FIG. 11C illustrates a FESEM image of exemplary MCF-7 cancer cell after US, consistent with one or more exemplary embodiments of the present disclosure.
Figure 11D:
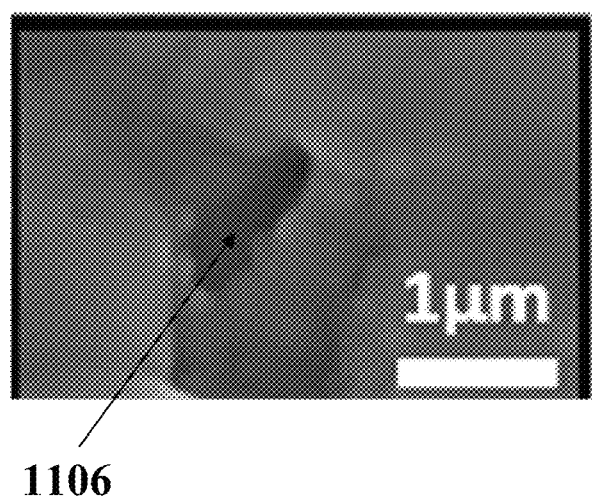
FIG. 11D illustrates a magnified FESEM image of exemplary sonopore formed in exemplary MCF-7 cancer cell after US, consistent with one or more exemplary embodiments of the present disclosure.

In addition, FESEM images were taken from all of the cells after electrochemically supported US. FIG. 11A shows field emission scanning electron microscopy (FESEM) image of exemplary MCF-10A normal cell 1100 after US, consistent with one or more exemplary embodiments of the present disclosure. It may be seen that exemplary sonopore 1102 was formed in exemplary MCF-10A normal cell 1100 after US. FIG. 11B shows a magnified FESEM image of exemplary sonopore 1102 formed in exemplary MCF-10A normal cell 1100 after US, consistent with one or more exemplary embodiments of the present disclosure. FIG. 11C shows a FESEM image of exemplary MCF-7 cancer cell 1104 after US, consistent with one or more exemplary embodiments of the present disclosure. It may be seen that exemplary sonopore 1106 was formed in exemplary MCF-7 cancer cell 1104 after US. FIG. 11D shows a magnified FESEM image of exemplary sonopore 1106 formed in exemplary MCF-7 cancer cell 1104 after US, consistent with one or more exemplary embodiments of the present disclosure. More extensive area of exemplary sonopore 1102 formed in healthy cells (MCF-10A) in comparison to exemplary sonopore 1106 formed in exemplary MCF-7 cancer cell 1104 may be a possible reason for more difference in the electrochemical response of the stimulated healthy MCF-10A cells. More extensive sonopores in stimulated healthy MCF-10A cells may cause more change in ion exchanges of stimulated healthy MCF-10A cells after US in comparison with MCF-7 cancer cell.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for detecting cancer cells, comprising:
preparing an electrochemical-ultrasonic system, comprising:
fabricating an electrochemical biosensor, the electrochemical biosensor comprising an integrated three-electrodes array patterned on a nanoroughened surface of a substrate, the integrated three-electrodes array comprising a working electrode, a counter electrode, and a reference electrode;

culturing a plurality of biological cells on the electrochemical biosensor comprising attaching the plurality of biological cells onto the working electrode by placing the electrochemical biosensor in a medium solution, the medium solution comprising a cell culture solution of the plurality of biological cells;

connecting the electrochemical biosensor with the plurality of cultured cells to an electrochemical stimulator-analyzer system, the electrochemical stimulator-analyzer system configured to measure electrochemical responses; and exposing the electrochemical biosensor with the plurality of cultured cells to an ultrasonic system;

generating a plurality of microbubbles on the electrochemical biosensor with the plurality of cultured cells comprising electrolysis of the medium solution by applying an instantaneous electrical potential in the medium solution utilizing a cyclic voltammetry technique using the electrochemical stimulator-analyzer system, applying the instantaneous electrical potential in the medium solution comprising applying a DC signal with a voltage between −2 V and −0.5 V for a time duration less than 1 seconds on the biosensor with the plurality of cultured cells;

measuring a first electrochemical response from the electrochemical biosensor with the plurality of cultured cells using the electrochemical stimulator-analyzer system, the first electrochemical response comprising an electrochemical response of the plurality of cultured cells;

forming a plurality of stimulated cells on the electrochemical biosensor by applying ultrasonic waves to the plurality of cultured cells and the plurality of microbubbles using the ultrasonic system;

measuring a second electrochemical response from the electrochemical biosensor with the plurality of stimulated cells using the electrochemical stimulator-analyzer system, the second electrochemical response comprising an electrochemical response of the plurality of stimulated cells; and detecting presence of cancer cells responsive to a difference between the first electrochemical response and the second electrochemical response being less than a threshold.

2. A method for detecting cancer cells, comprising:

forming a plurality of cultured cells on an electrochemical biosensor by placing the electrochemical biosensor in a medium solution comprising a cell culture solution of a plurality of biological cells;

measuring a first electrochemical response from the electrochemical biosensor with the plurality of cultured cells, the first electrochemical response comprising a first cyclic voltammetry (CV) pattern comprising a first set of measured electrical currents versus a range of applied electrical potentials comprising a respective first current peak;

generating a plurality of microbubbles on the electrochemical biosensor with the plurality of cultured cells comprising electrolysis of the medium solution by applying an instantaneous electrical potential to the electrochemical biosensor with the plurality of cultured cells via a cyclic voltammetry technique using an electrochemical stimulator-analyzer system;

forming a plurality of stimulated cells on the electrochemical biosensor by applying ultrasonic waves to the plurality of cultured cells and the plurality of microbubbles using an ultrasonic system;

measuring a second electrochemical response from the electrochemical biosensor with the plurality of stimulated cells, the second electrochemical response comprising a second CV pattern comprising a second set of measured electrical currents versus the range of applied electrical potentials comprising a respective second current peak; and detecting presence of cancer cells responsive to a difference between the first electrochemical response and the second electrochemical response being less than a threshold, the difference between the first electrochemical response and the second electrochemical response comprising a peak to peak $$\frac{\Delta I}{I},$$

the peak to peak $$\frac{\Delta I}{I}$$

being defined by:
peak to peak $$\frac{\Delta I}{I} = \frac{I_{US\,off} - I_{US\,on}}{I_{US\,off}}$$

where $I_{USoff}$ comprises the first current peak and $I_{USon}$ comprises the second current peak.

3. The method of claim 2, wherein detecting the presence of cancer cells comprises detecting presence of breast cancer cells responsive to the peak to peak $$\frac{\Delta I}{I}$$

being less than the threshold comprising a value of 0.15.

4. The method of claim 3, wherein:
the threshold comprises a value of 0.05 for the ultrasonically stimulating of the plurality of cultured cells with an intensity of less than 1 W/cm$^2$ and a duration of less than 5 seconds, and
the threshold comprises a value of 0.15 for the ultrasonically stimulating of the plurality of cultured cells with an intensity of more than 1 W/cm$^2$ and a duration of less than 5 seconds.

5. The method of claim 2, wherein each of the measuring the first electrochemical response from the electrochemical biosensor with the plurality of cultured cells and measuring the second electrochemical response from the electrochemical biosensor with the plurality of stimulated cells comprises measuring an electrochemical response via the cyclic voltammetry technique using the electrochemical stimulator-analyzer system.

6. The method of claim 5, wherein the electrochemical stimulator-analyzer system comprises a potentiostat.

7. The method of claim 2, wherein forming the plurality of cultured cells on the electrochemical biosensor comprises:
   placing the electrochemical biosensor at the bottom of a chamber; and
   filling the chamber with the medium solution.

8. The method of claim 2, wherein generating the plurality of microbubbles on the electrochemical biosensor with the plurality of cultured cells comprises applying a DC signal with a voltage between −2 V and −0.5 V for a time duration less than 1 seconds on the biosensor with the plurality of cultured cells using a potentiostat device.

9. The method of claim 2, wherein forming the plurality of stimulated cells on the electrochemical biosensor comprises:
   ultrasonically stimulating the plurality of cultured cells responsive to applying ultrasonic waves to the plurality of cultured cells on the electrochemical biosensor in the medium solution; and
   inducing an acoustic cavitation in the plurality of cultured cells by the plurality of microbubbles responsive to applying ultrasonic waves to the plurality of microbubbles on the electrochemical biosensor in the medium solution.

10. The method of claim 2, wherein forming the plurality of stimulated cells on the electrochemical biosensor comprises:
    exposing the medium solution containing the electrochemical biosensor with the plurality of cultured cells to the ultrasonic system; and
    applying ultrasonic waves to the medium solution with a frequency range between 10 KHz and 100 KHz for a time duration between 2s and 10 s to the plurality of cultured cells using the ultrasonic system.

11. The method of claim 10, wherein exposing the medium solution containing the electrochemical biosensor with the plurality of cultured cells to the ultrasonic system comprises placing an ultrasonic horn above the electrochemical biosensor with the plurality of cultured cells, the ultrasonic horn being connected to an ultrasonic generator.

12. The method of claim 10, wherein ultrasonic ultrasonically stimulating the plurality of cultured cells comprises applying ultrasonic waves using the ultrasonic system with an intensity between 0.5 w/cm$^2$ and 5 w/cm$^2$.

* * * * *